United States Patent
Venkatramesh et al.

(10) Patent No.: US 8,568,798 B2
(45) Date of Patent: Oct. 29, 2013

(54) PRODUCTION AND EXTRACTION OF PROCYANIDINS FROM PLANT CELL CULTURES

(75) Inventors: Mylavarapu Venkatramesh, Carmel, IN (US); D. Ry Wagner, Pleasant Hill, OR (US); Sonia Lall, Portland, IN (US); Frederic Y. Lejard, Arradon (FR); Sung-Yong H. Yoon, Lake Oswego (KR)

(73) Assignee: DianaPlantSciences, S.A.S., Rennes (FR)

( * ) Notice: Subject to any disclaimer, the term of this patent is extended or adjusted under 35 U.S.C. 154(b) by 0 days.

(21) Appl. No.: 13/262,456

(22) PCT Filed: May 4, 2009

(86) PCT No.: PCT/US2009/042722
§ 371 (c)(1),
(2), (4) Date: Sep. 30, 2011

(87) PCT Pub. No.: WO2010/114567
PCT Pub. Date: Oct. 7, 2010

(65) Prior Publication Data
US 2012/0021080 A1    Jan. 26, 2012

Related U.S. Application Data

(60) Provisional application No. 61/166,591, filed on Apr. 3, 2009.

(51) Int. Cl.
*A61K 36/00* (2006.01)
*C12N 5/00* (2006.01)

(52) U.S. Cl.
USPC .......................... 424/725; 424/769; 435/410

(58) Field of Classification Search
None
See application file for complete search history.

(56) References Cited

U.S. PATENT DOCUMENTS

| | | | |
|---|---|---|---|
| 4,306,022 A * | 12/1981 | Kinsella et al. ............... 435/134 |
| 4,545,147 A | 10/1985 | Janick et al. | |
| 5,407,816 A | 4/1995 | Bringi et al. | |
| 5,554,645 A | 9/1996 | Romanczyk, Jr. et al. | |
| 5,853,728 A | 12/1998 | Tanabe et al. | |
| 5,871,979 A | 2/1999 | Choi et al. | |
| 6,194,020 B1 | 2/2001 | Myers et al. | |
| 6,225,338 B1 | 5/2001 | Romanczyk, Jr. et al. | |
| 6,312,753 B1 | 11/2001 | Kealey et al. | |
| 6,589,765 B1 | 7/2003 | Choi et al. | |
| 6,627,232 B1 | 9/2003 | Hammerstone, Jr. et al. | |
| 6,638,971 B2 | 10/2003 | Romanczyk, Jr. et al. | |
| 6,998,417 B2 | 2/2006 | Romanczyk, Jr. et al. | |
| 7,122,574 B2 | 10/2006 | Romanczyk, Jr. et al. | |
| 7,264,951 B1 | 9/2007 | Bringi et al. | |
| 7,314,634 B2 | 1/2008 | Hernandez et al. | |
| 7,320,797 B2 | 1/2008 | Gupta | |
| 2001/0047524 A1 * | 11/2001 | Guiltinan et al. ............. 800/298 |
| 2003/0203962 A1 | 10/2003 | Howell et al. | |
| 2004/0162338 A1 | 8/2004 | Schmitz | |
| 2005/0089592 A1 | 4/2005 | Chevaux et al. | |
| 2006/0021084 A1 | 1/2006 | Abraham et al. | |
| 2006/0078872 A1 | 4/2006 | Taguchi et al. | |
| 2007/0075020 A1 | 4/2007 | Kelm et al. | |
| 2007/0148107 A1 | 6/2007 | Sies et al. | |
| 2008/0003314 A1 | 1/2008 | Ochiai et al. | |
| 2008/0060093 A1 | 3/2008 | Zieler et al. | |
| 2008/0274234 A1 | 11/2008 | Miller | |
| 2010/0189829 A1 | 7/2010 | Bernaert et al. | |
| 2010/0236143 A1 | 9/2010 | Florin et al. | |

FOREIGN PATENT DOCUMENTS

| WO | WO 97/36497 | 10/1997 |
|---|---|---|
| WO | WO 99/00487 | 1/1999 |
| WO | WO2006/117465 | 11/2006 |

OTHER PUBLICATIONS

Marziah et al, Production of polyphenols in cultured tissues of cocoa, *Theobroma cacao*. Current plant science and biotechnology in agriculture, 1993. vol. 15 p. 328-331.*

Jalal et al, Polyphenols of mature plant, seedling and tissue cultures of *Thebroma cacao*, Phytochemistry (1977) vol. 16, No. 9, pp. 1377-1380.*

International Search Report issued Jun. 23, 2009, Application No. PCT/US09/42722, filed May 4, 2009.

Chinese Office Action dated Aug. 31, 2012, issued in Chinese Application No. 200980159092.5, filed Nov. 3, 2011.

Supplementary EP Search Report dated Aug. 23, 2012 issued in EP 09842834, filed May 4, 2009.

International Search Report and Written Opinion dated Feb. 14, 2012, Application No. PCT/US2011/054648, filed Oct. 3, 2011.

Luisa F. Rojas et al., *Total Polyphenols Analysis of Mature Seeds and Tissue Cultures of Some Colombians Coloa Varieties*, Actualidades Biologicas, vol. 30, No. 89, Jul. 2008, pp. 117-123.

(Continued)

*Primary Examiner* — Qiuwen Mi
(74) *Attorney, Agent, or Firm* — Workman Nydegger

(57) ABSTRACT

Provided herein are methods of making cocoa polyphenol preparations, which methods comprises harvesting cocoa polyphenols, for example, procyanidins, from the cell suspension culture. In examples of these methods, the resultant cocoa polyphenol preparation is substantially (or in some cases, completely) free of detectable caffeine and theobromine, and more generally substantially free of xanthine alkaloids. Methods of producing a cell suspension culture of cacao cells are also described, including cell suspension cultures useful for making cocoa polyphenol and, more specifically, procyanidin preparations. *Theobroma* and *Herrania* sp cell suspension cultures and cocoa polyphenol preparations made therefrom are also provided, in particular xanthine alkaloid-free (or caffeine- and/or theobromine-free) cocoa polyphenol preparations.

9 Claims, 13 Drawing Sheets

(56) References Cited

OTHER PUBLICATIONS

Jorge M. Richardo da Silva et al., *Oxygen Free Radical Scavenger Capacity in Aqueous Models of Different Procyanidins from Grape Seeds*, Journal Agric. Food Chem., vol. 39, 1991, pp. 1549-1552.

J.A. Bomser et al., *Inhibition of TPA-induced Tumor Promotion in CD-1 Mouse Epidermis by a Polyphenolic Fraction from Grape Seeds*, Cancer letters, vol. 135, 1991, pp. 151-157.

Jifu Zhao et al., *Anti-Tumor-Promoting Activity of a Polyphenolic Fraction Isolated From Grape Seeds in the Mouse Skin Two-Stage Initiation-Promotion Protocol and Identification of Procyanidin B5-3'-Gallate as the Most Effective Antioxidant Constituent*, Carcinogenesis, vol. 20, No. 9, 1999, pp. 1737-1745.

B.M. Tijburg et al., *Effects of Green Tea, Black Tea and Dietary Lipophilic Antioxidants on LDL Oxidizability and Atherosclerosis in Hypercholesterolaemic Rabbits*, Atherosclorosis, vol. 135, 1997, pp. 37-47.

Jun Yamakoshi et al., *Proanthocyanidin-Rich Extract from Grade Seeds Attenuates the Development of Aortic Atherosclerosis in Cholesterol-fed Rabbits*, Atherosclerosis, vol. 42, 1999, pp. 139-149.

D. Steinberg, *Antioxidants in the Prevention of Human Atherosclerosis. Summary of the Proceedings of a National Heart, Lung, and Blood Institute Workshop*, Circulation, vol. 85, 1992, pp. 2337-2344.

L. J. Porter et al., *CACAO Procyanidins: Major Flavanoids and Identification of Some Minor Metabolites*, Phytochemistry, vol. 30, No. 5, 1991, pp. 1657-1663.

Chiaki Sanbongi et al., *Antioxidative Polyphenols Isolated from Theobroma cacao*, Journal Agric. Food Chem., vol. 46, 1998, pp. 454-457.

Gary E. Adamson et al., *HPLC Method for the Quantification of Procyanidins in Cocoa and Chocolate Samples and Correlation to Total Antioxidant Capacity*, Journal Agric. Food Chem., vol. 47, 1999, pp. 4184-4188.

Michael J. Muhitch et al., *Isolation and Identification of the Phenols of Paul's Scarlet Rose Stems and Stem-Derived Suspension Cultures*, Plant Physiol., vol. 75, 1984, pp. 592-595.

Nariyuki Ishikura et al., *Procyanidins and Catechin From Callus and Cell Suspension Cultures of Cryptomeria japonica*, Agric. Biol. Chem., vol. 47, No. 2, 1983, pp. 421-423.

H. A. Stafford et al., *The Procyanidins of Douglas Fir Seedlings, Callus and Cell Suspension Cultures Derived from Cotyledons*, Phytochemistry, vol. 19, 1980, pp. 131-135.

A. Decendit et al., *Condensed Tannin and Anthocyanin Production in Vitis vinifera Cell Suspension Cultures*, Plant Cell Reports, vol. 15, 1996, pp. 762-765.

Pierre Waffo Teguo et al., *Trans-Resveratrol-0-β-Glucoside (Piceid) in Cell Suspension Cultures of Vitis vinifera*, Phytochemustry, vol. 42, No. 6, 1996, pp. 1591-1593.

L. Alemanno et al., *Histology of Somatic Embryogenesis from Floral Tissues Cocoa*, Plant Cell, Tissue and Organ Culture, vol. 46, 1996, pp. 187-194.

L. Alemanno et al., *A Comparison Between Theobroma cacao L. Zygotic Embryogenesis and Somatic Embryogenesis from Floral Explants*, In Vitro Cell Dev. Biol. Plant, vol. 33, Jul.-Aug.-Sep. 1997, pp. 163-172.

Zhijian Li et al., *Somatic Embryogenesis and Plant Regeneration from Floral Explants of Cacao (Theobroma cacao L.) Using Thidiazuron*, In Vitro Cell Dev. Biol. Plant, vol. 34, Oct.-Dec. 1998, pp. 293-299.

Siela N. Maximova et al., *Efficiency, Genotypic Variability, and Cellular Origin of Primary and secondary Somatic Embryogenesis of Theobroma cacao L.*, In Vitro Cell Dev. Biol. Plant, vol. 38, May-Jun. 2002, pp. 252-259.

T.R.H. Hall & H.A. Collin, *Initiation and Growth of Tissue Cultures of Theobroma cacao*, Annals of Bot., vol. 39, 1975, pp. 555-70.

Mahbubul A. F. Jalal & Hamish A. Collin, *Polyphenols of Mature Plant, Seedling and Tissue Cultures of Theobroma cacao*, Phytochemistry, vol. 16, 1977, pp. 1377-1380.

M.A.F. Jalal & H.A. Collin, *Secondary Metabolism in Tissue Cultures of Theobroma cacao*, New Phytol., vol. 83, 1979, pp. 343-349.

C.H. Tsai et al., *Cocobean Tissue Culture: Lipid Composition and Fatty Acid Metabolism*, Journal of Food Science, vol. 47, 1982, pp. 768-773.

Ming-Che Wen et al., *Cocoa Bean Cell and Embryo Culture*, Journal Am. Oil Chemist's Soc., vol. 16, No. 11, Nov. 1984, pp. 1720-1724.

Karen A. Gurney et al., *Purine Alkaloid Production and Accumulation in Cocoa Callus and Suspension Cultures*, Journal of Experimental Botany, vol. 43, No. 251, Jun. 1992, pp. 769-775.

Sumana Neera et al., *Tannin Production in Sapium sebiferum Callus Cultures*, Phytochemistry, vol. 31, No. 12, 1992, pp. 4143-4149.

J.E. Meyer et al., *Anthocyanin Production from Vaccinium pahalae: Limitations of the Physical Microenvironment*, Journal of Biotechnology, vol. 93, 2002, pp. 45-57.

V. C. Quesnel, *Fractionation and Properties of the Polymeric Leucocyanidin of the Seeds of Theobroma cacao*, Phytochemistry, vol. 7, 1968, pp. 1583-1592.

Mattheus F.A. Goosen, *Large-scale Insect Cell Culture: Methods, Applications and Products*, Current Opinion in Biotechnology 1991, vol. 3, 1991, pp. 365-369.

N. T. Thanh et al., *Effect of Carbon Dioxide on Cell Growth and Saponin Production in Suspension Cultures of Panax Ginseng*, Biologia Plantarum, vol. 50, No. 4, 2006, pp. 752-754.

Jeffrey L.Tate et al., *Plant Cell Growth Under Different Levels of Oxygen and Carbon Dioxide*, Plant Cell Reports, vol. 10, 1991, pp. 22-25.

T. Swain et al., *The Phenolic Constituents of Prunus domestica*, J. Sci. Food Agric. vol. 10, 1959, pp. 63-68.

Lawrence J. Porter et al., *The Conversion of Procyanidins and Prodelphinidins to Cyanidin and Delphinidin*, Phytochemistry, vol. 25, No. 1, 1986, pp. 223-230.

Beum Jun Kim et al., *Effect of Subculture and Elicitation of Instability of Taxol Production in Taxus sp. Suspension Cultures*, Biotechnol Prog., vol. 20, No. 6, 2004, pp. 1666-1673.

Lazarus et al., *High-Performance Liquid Chromatography/Mass Spectrometry Analysis of Proanthocyanidins in Foods and Beverages*, Journal of Agric. Food Chem., vol. 47, 1999, pp. 3693-3701.

Giacometti, *Amazonia and Caribbean Agriculture*, Chapter 19, 1994, 13 pages.

Nariyuki Ishikura et al., *Procyanidins and Catechin from Callus and Cell Suspension Cultures of Cryptomeria japonica*, Agric. Biol. Chem., 47(2), 1983, pp. 421-423.

Valeria Creaser Pence et al., *Initiation and Development of Asexual Embryos*, J. Am. Soc. Hort. Sci. vol. 104, 1979, pp. 145-148.

Antonio Figueira et al., *Development of Nucellar Somatic Embryos of Theobroma cacao*, Acta Hort., vol. 336, 1993, pp. 231-238.

M. R. Sondhal et al., Cacao Somatic Embryogenesis, Acta Hort., vol. 336, 1993, pp. 245-248.

Dicosmo & Misawa, *Plant Cell Culture Secondary Metabolism, Chapter 2: Large-Scale Production of Seconardy Metabolites by Plant Cell Cultures*, Boca Raton, Florida, Crc Press LLC., 1996, pp. 11-44.

Mattheus F.A. Goosen, *Large-scale Insect Cell Culture: Methods, Applications and Products*, Current Opinion in Biotechnology, vol. 2, 1991, pp. 365-369.

Payne et al., *Plant Cell and Tissue Culture in Liquid Systems: Elicitors*, 1995, New York, John Wiley & Sons, Inc., pp. 333.

Guohua Cao et al., *Oxygen-Radical Absorbance Capacity Assay for Antioxidants*, Free Radical Biology Med., 14(3) 1993, pp. 303-11.

* cited by examiner

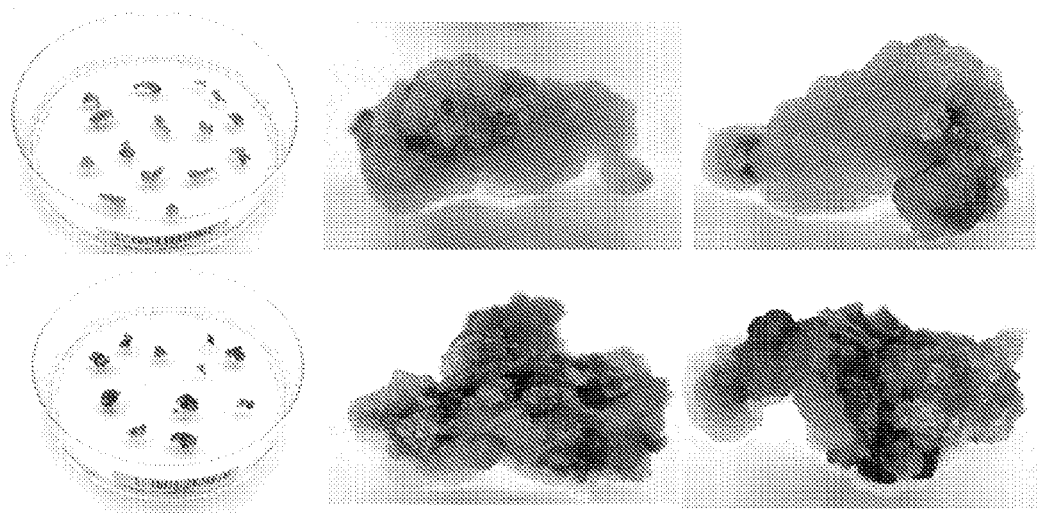
FIG. 1
FIG. 2
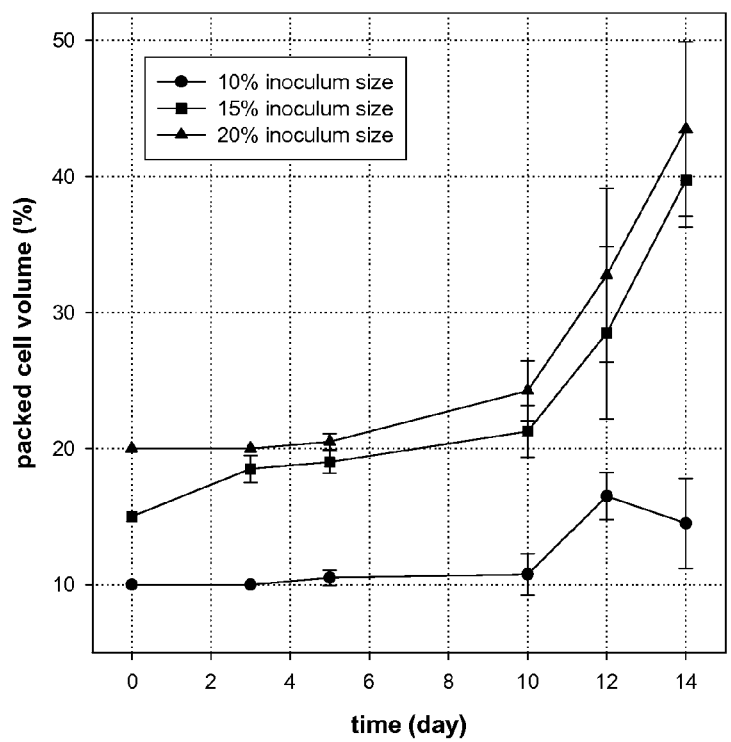

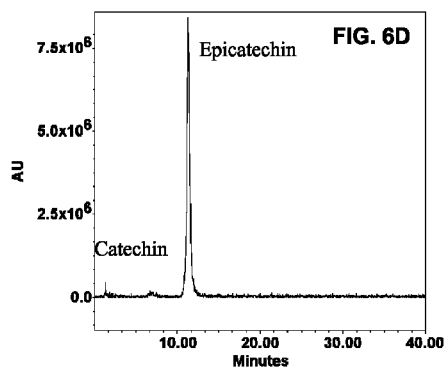
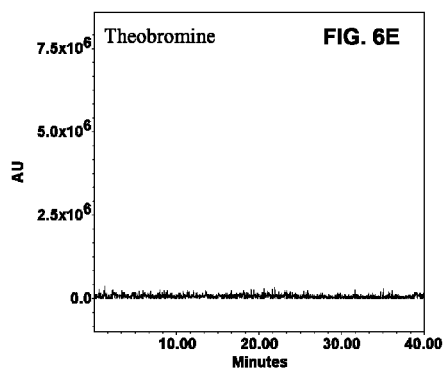
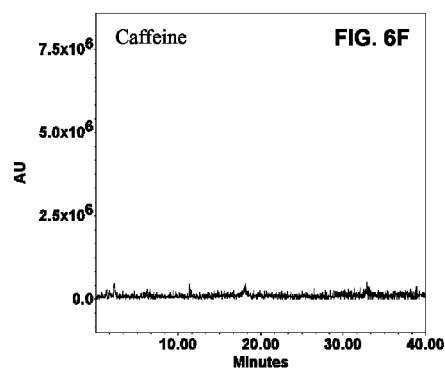

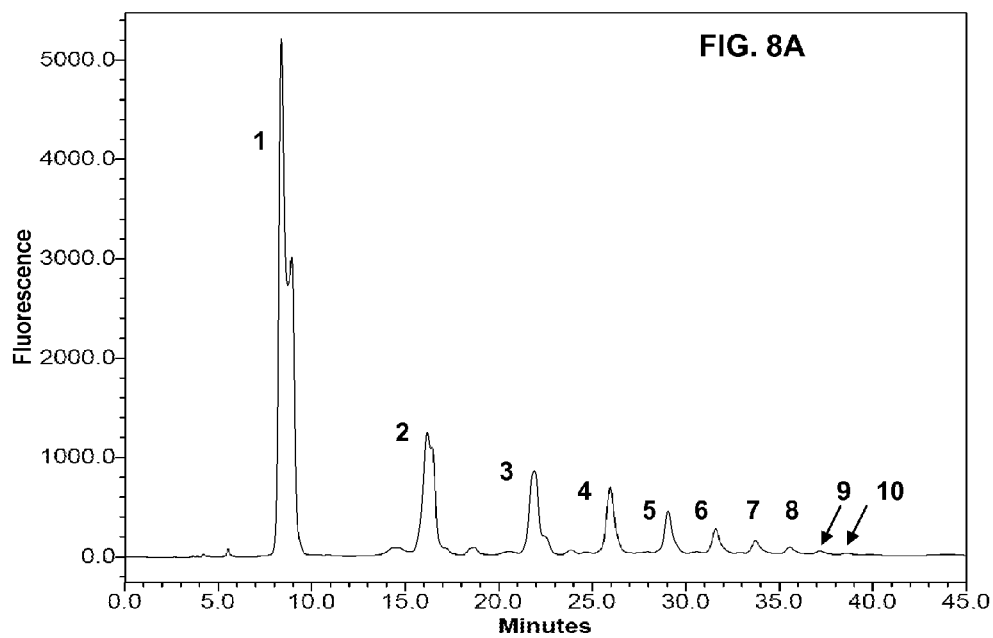
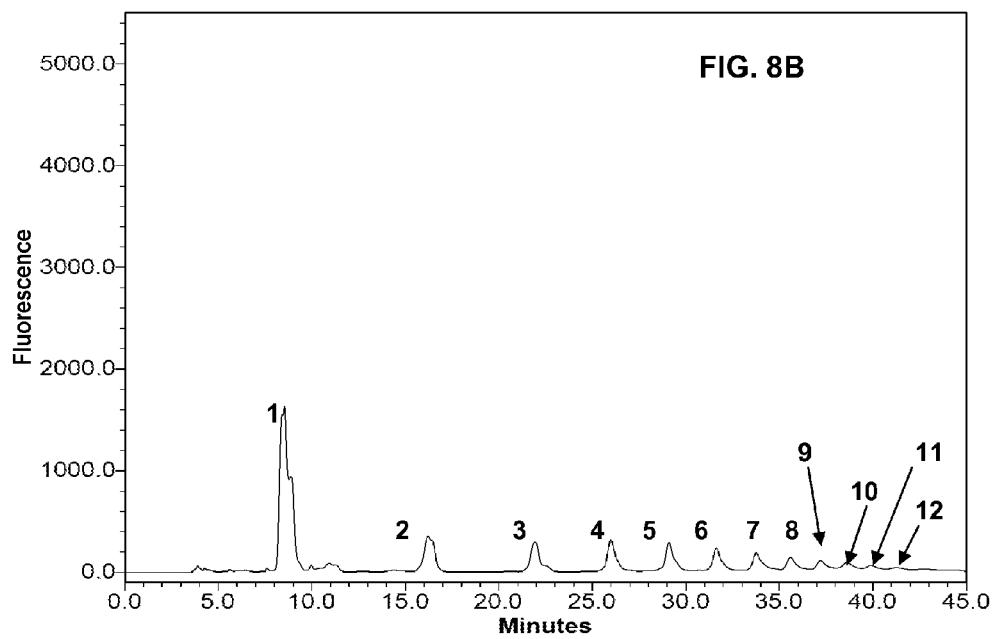

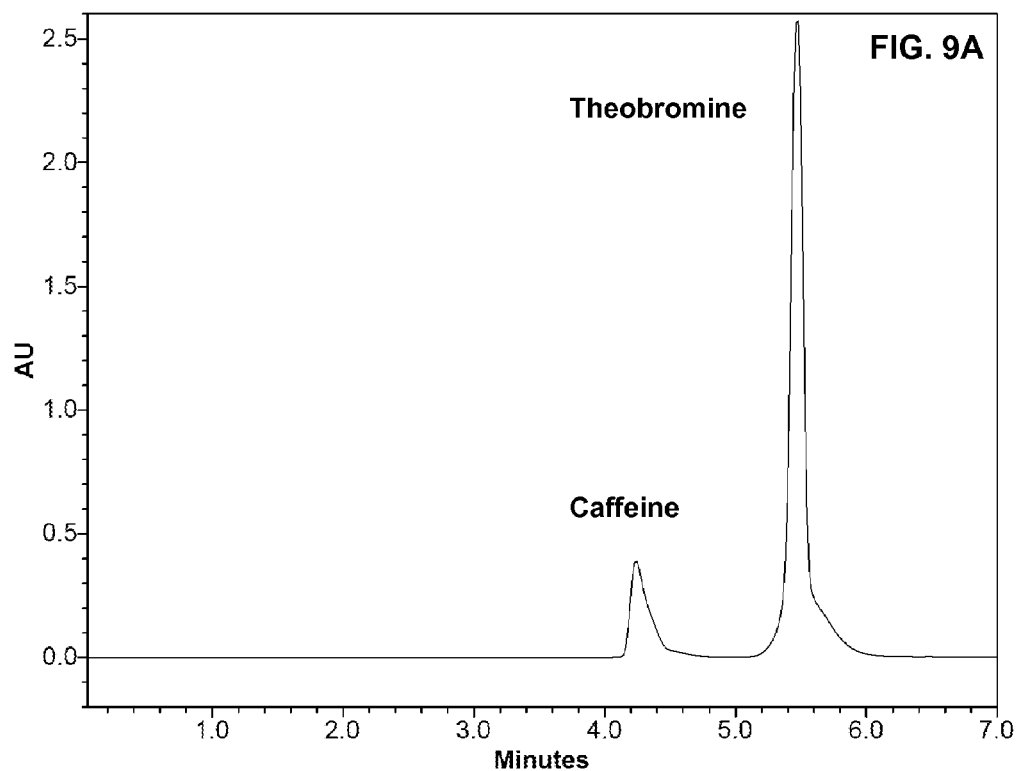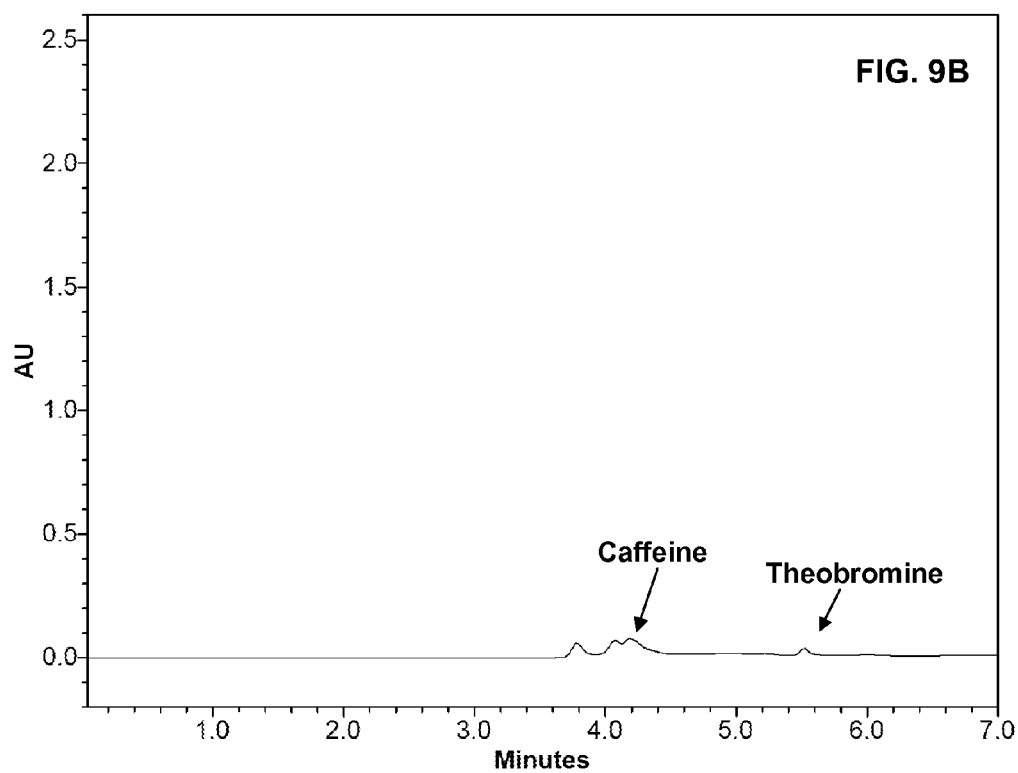

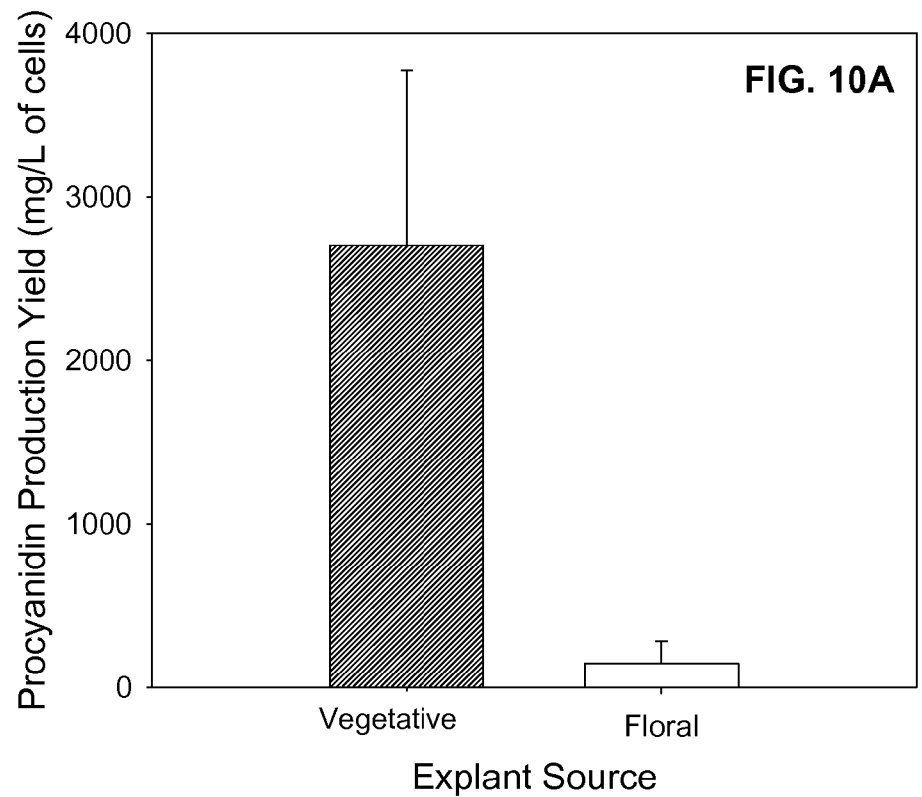
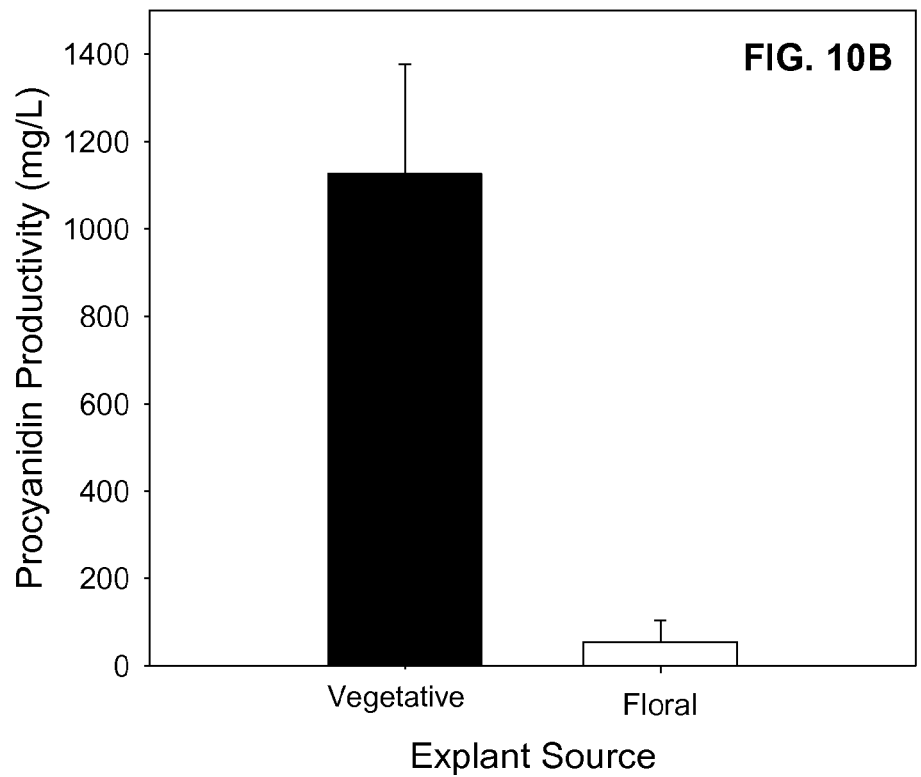

PRODUCTION AND EXTRACTION OF PROCYANIDINS FROM PLANT CELL CULTURES

CROSS-REFERENCE TO RELATED APPLICATION

This application claims the benefit of U.S. Provisional Application No. 61/166,591 filed Apr. 3, 2009, which is incorporated herein by reference in its entirety.

FIELD OF THE DISCLOSURE

The present disclosure relates to methods for developing cell cultures of cacao tissue. The disclosure also relates to methods to select for cell lines that produce high levels of procyanidins and extracting the same from the cell cultures to produce food ingredients, food additives, therapeutic compositions, or cosmetic compositions. The disclosure further relates to novel culture media such as liquid media for growing cell suspension cultures of cacao cells and liquid media compositions for enhanced procyanidin production by such suspension cells.

BACKGROUND OF THE DISCLOSURE

Polyphenols are widely distributed in plants, fruits, and vegetables and have received considerable attention because of their physiological functions in human and animal health, including antioxidant, antimutagenic and cancer prevention activities (Salvia et al., *J. Agric. Food Chem.* 39: 1549-1552, 1991; Bomser et al., *Cancer Lett.,* 135: 151-157, 1999; Zhao et al., *Carcinogenesis,* 20: 1737-1745, 1999). Epidemiological studies have suggested that flavonoids, among the polyphenols, may reduce the risk of heart disease (Hertog et al., *Lancet:* 342: 1007-1011, 1993). Additionally, dietary flavan-3-ols and/or proanthocyanidins have been shown to reduce the incidence of atherosclerosis and coronary heart disease in experimental animals (Tijburg et al., *Atherosclorosis,* 135: 37-47, 1997; Yamakoshi et al., *Atherosclerosis,* 142: 139-149, 1999). One of the mechanisms responsible for these effects involves their inhibition of oxidation of low density lipoprotein (LDL) (Steinberg, *Circulation,* 85: 2337-2344, 1992).

The seeds of the cacao plant (*Theobroma cacao* L., Sterculiaceae) are known to be rich in polyphenols (Porter et al., *Phytochemistry,* 30: 1657-1663, 1991). Some of the antioxidant components of cacao liquor prepared from fermented and roasted cacao beans, which is a major ingredient of cocoa and chocolate products, have been characterized as flavan-3-ols and procyanidin oligomers (Sanbongi et al., *J. Agric. Food Chem.,* 46: 454-457, 1998; Adamson et al., *J. Agric. Food Chem.,* 47: 4184-4188, 1999).

Other species of *Theobroma* and other genera such as *Herrania* are also known sources of cocoa procyanidins. Twenty different species of *Theobroma* have been described but usually only 12 are accepted. Of these, nine are native to Amazonia, hence the center of genetic distribution appears to be the western half of the region (Giacometti, 1994, In "Neglected Crops: 1492 from a different perspective (J. E. Hernando Bermejo and J. Leon, Eds.) Plant Production and Protection Series No. 26, FAO, Rome, Italy, p205-209).

The genus *Theobroma* is typically neotropical and is distributed in the tropical rain forest in the Western Hemisphere between lat. 18° N and 15° S. The region with the most species is between Costa Rica and northeastern Colombia. Five sections and 20 species are recognized. *Theobroma grandiflorum* belongs to the section *Glossopetalum,* made up of 11 species; *Theobroma cacao* is the only species of the *Theobroma* section.

Four species of *Theobroma* have been described as producers of edible flesh: *Theobroma grandiflorum, Theobroma canumanense* Pires & Froes, *Theobroma subincanum* Martius, (Cupui in Brazil and Cacau de monte in Colombia) and *Theobroma tricolor* Humb. & Bonpl., which is a small tree distributed from western Amazonia to southern Mexico. Chocolate is also made from the seeds of these species (Giacometti, 1994, In "Neglected Crops: 1492 from a different perspective (J. E. Hernando Bermejo and J. Leon, Eds.) Plant Production and Protection Series No. 26, FAO, Rome, Italy, p205-209). It has been shown that beans of several species of *Theobroma* and *Herrania* produce similar procyanidins and that these compounds can be extracted from the beans (Romanczyk et al., WO 97/36497).

The polyphenols in cocoa beans are stored in the pigment cells of the cotyledons. Depending on the amount of anthocyanins in those pigmented cells, also called polyphenol-storage cells, they are white to deep purple. Three groups of polyphenols can be distinguished in these cells: catechins or flavan-3-ols (~37%), anthocyanins (~4%), and proanthocyanidins (~58%). The main catechin is (−)-epicatechin which constitutes up to 35% of total polyphenol content. Procyanidins (commonly referred to as proanthocyanidins) are mainly flavan-3,4-diols, that are 4→8 or 4→6 bound to condensed dimmers, trimers, or oligomers with epicatechin as the main extension sub-unit (Romanczyk et al., WO 97/36497).

The total amount of soluble polyphenols in the dried fat-free mass of fresh cocoa beans is 15 to 20% (equaling ~6% in air dried cocoa beans, containing 54% fat and 6% moisture), and in fermented beans ~5%. Thus, one of the major drawbacks of using cocoa beans as a source of polyphenols is that most of the polyphenols are lost during processing of the beans. Other steps such as roasting and defatting also lead to losses. Thus, cocoa powder has less than 10% of the total polyphenols found in fresh beans. Another problem for using cocoa beans is the limited growth range for the plant, *Theobroma cacao.* It grows only in warm, moist climates in areas about 20° latitude north and south of the equator. This makes it difficult to preserve the polyphenol content of the beans during storage and transportation to areas where they can be processed and polyphenols extracted.

Plant cell culture is an attractive alternative to overcome these problems. Plant cell cultures have recently been used for the isolation of flavonoids. In the case of procyanidins, several groups were able to isolate particular compounds from cultures. For example, 4→8 linked (−)-epicatechin-(+)-catechin and gallic acid have been isolated from a *Rosa* culture (Muhitch & Fletcher, *Plant Physiol.,* 75:592-595, 1984). Suspension cultures and calluses of *Cryptomeria japonica* were found to produce as much as 26% of dry weight as procyanidins (Teramoto & Ishikura, *Bot. Mag. Tokyo* 98: 171-179, 1985; Ishikura & Teramoto, *Agric. Biol. Chem.* 47: 421-423, 1983), and *Pseudotsuga mensiesii* suspension cultures produced as much as 40% of their dry weight as procyanidins (Stafford & Cheng, *Phytochemistry* 19: 131-135, 1980). Reports have also shown the production of procyanidins in cell suspension cultures of *Vitis vinifera* (Decendit & Merillon, *Plant Cell Rep.* 15: 762-765, 1996; Waffo-Teguo et al., *Phytochem.* 42:1591-1593, 1996).

Tissue culture research in *Theobroma cacao* has focused on somatic embryogenesis, which has been developed in several laboratories for the purpose of clonal propagation of the plant. The first report of *Theobroma cacao* somatic embryogenesis was by Esan in 1977 (*Proc. 5$^{th}$ Int. Cacao Res.*

Conf. 1975. Ibadan: Cacao Res. Inst. Nigeria, 1977: 116-125, 1977), who described a method using immature zygotic embryo tissue explants. Similar methods were later reported by others (Pence et al., *J. Am. Soc. Hort. Sci.* 104: 145-148, 1979; Villalobos & Aguilar, *Abstr. VII Int. Congr. Plant Tissue and Cell Cult., Amsterdam, Int. Assoc. for Plant Tissue Culture*, pp 140, 1990). Later studies were focused on development of tissue culture methods from somatic tissues including leaves (Litz, In Dimick, P.S., Ed., *Cacao biotechnology symposium. The Pennsylvania State University Press*, University Park, Pa., pp 111-120, 1986), nucellus (Chatelet et al., *C.R. Acad. Sci., Paris* 315: 55-62, 1992; Figueira & Janick, *Acta Hort.* 336: 231-238, 1993; Sondhal et al., *Acta Hort.* 336: 245-248, 1993), and floral explants including petals and staminodes (Lopez-Baez et al., *C.R. Acad. Sci., Paris* 316: 579-584, 1993; Alemanno et al., *Plant Cell Tiss. Organ Cult.* 46: 187-194, 1996; Alemanno & Michaux-Ferriere, *In Vitro Cell Dev. Biol. Plant* 33: 163-172, 1997). These early methods, though successful, were not applicable to all genotypes and the frequency of regenerated plants was low. More efficient methods capable of propagating a wide range of genotypes were also developed (Li et al., *In Vitro Cell Dev. Biol. Plant* 34: 293-299, 1998; Maximova et al., *In Vitro Cell Dev. Biol. Plant* 38: 252-259, 2002). However, all the described methods, while using tissue culture methods to produce somatic embryos, did not teach methods to raise suspension cells.

There is limited amount of published work on developing cell cultures of *Theobroma cacao*. Most of this work was in the 1970's and 1980's (Hall & Collin, *Annals of Bot.* 39: 555, 1975; Jalal & Collin, *Phytochem.* 16: 1377-1380, 1977; Jalal & Collin, *New Phytol.* 83: 343-349, 1979; Tsai et al., *J. Food Sci.* 47: 768-773, 1982; Wen et al., *J. Am. Oil Chemist's Soc.* 16: 1720-1724, 1984). Of these, only a few have studied flavonoids in cell cultures of *Theobroma cacao*. For instance, Jalal and Collin (1979) reported that the flavonoid compositions of the callus and cell suspensions were similar and much less varied than that of the original intact cotyledon. Both tissue cultures contained (−)-epicatechin, leucocyanidins, caffeic and coumaric acids. The methylated purines, theobromine and caffeine, could not be detected in the tissue cultures. However, Gurney et al. (*J. Expt. Bot.* 43: 769-775, 1992) reported that callus and suspension cultures of *Theobroma cacao* produced caffeine, theobromine and theophylline at concentrations about 10% of those found in vivo.

None of the prior art has reported the formation of oligomeric procyanidins, which in recent years have been shown to have the greatest bioefficacy. Jalal and Collin (*New Phytol.* 83: 343-349, 1979) reported the detection of leucocyanidins in cell cultures of *Theobroma cacao*. However, based on the methods used to detect the compounds it was not possible to characterize the nature or size of the leucocyanidins. Further, tissue culture methods have not been described for other species of *Theobroma* or *Herrania*.

SUMMARY

Development of methods for generating cell cultures that can produce high yields of procyanidins and development of methods for efficiently extracting these compounds from the cultures can significantly increase the production of these valuable compounds and will not require the burdensome task of developing novel methods for processing cocoa beans to reduce losses of procyanidins. Such cell cultures and methods are described herein.

Provided herein are methods of preparing a substantially xanthine alkaloid-free cocoa polyphenol preparation, which methods comprise growing *Theobroma* or *Herrania* cells in suspension culture for a time sufficient and under conditions sufficient to result in production of cocoa polyphenols, and harvesting cocoa polyphenols from the cell suspension culture. In particular embodiments of the disclosed methods, *Theobroma* or *Herrania* cells are grown in suspension culture for a time sufficient and under conditions sufficient to result in production of cocoa procyanidins (for example, oligomeric procyanidins), and harvesting cocoa procyanidins from the cell suspension culture. In examples of these methods, the resultant cocoa polyphenol (or procyanidin) preparation is substantially (or in some cases, completely) free of detectable caffeine and/or theobromine.

Also provided are methods of producing a cell suspension culture of cacao cells. Examples of these methods involve growing callus from an immature *Theobroma* sp. floral explant or from *Theobroma* sp. vegetative material on solid growth medium; selecting a rapidly growing cell line from the *Theobroma* sp. callus culture; and initiating the cell suspension culture by inoculating the rapidly growing cell line into liquid medium. By way of example, the immature *Theobroma cacao* floral explant is in some cases selected from staminode, sepal and petal base explants. In other specific, non-limiting examples, the *Theobroma* sp. vegetative material is selected from young or mature leaves, stems, meristem, nodes, or internodes.

Also provided is a substantially xanthine alkaloid-free cocoa polyphenol preparation produced using any one of the methods described herein. In particular embodiments, the cocoa polyphenol preparation lacks detectable levels of xanthine alkaloids (the preparation is xanthine alkaloid-free). In other embodiments, the addition of supplemental glucose to the suspension culture, at the end of the exponential growth stage, augments procyanidin production.

Also contemplated herein are *Theobroma* or *Herrania* cell suspension cultures produced by any one of the described methods, as well as use of these cell suspension cultures to produce cocoa polyphenols (for example, procyanidins). Cocoa polyphenol preparations comprising a mixture of cocoa polyphenols and substantially free of caffeine and/or theobromine are provided herein as well, which preparations are extracted from a *Theobroma* or *Herrania* cell suspension culture. In specific, non-limiting examples, the cocoa polyphenol preparations comprise procyanidins (for example, oligomeric procyanidins) and are substantially free of caffeine and/or theobromine. In particular, non-limiting embodiments, the cocoa polyphenols described herein can be used in dietary, cosmetic, therapeutic, or veterinary compositions.

The foregoing and other objects, features, and advantages will become more apparent from the following description, which proceeds with reference to the accompanying figures.

BRIEF DESCRIPTION OF THE DRAWINGS

FIG. 1 is a photograph of rapidly growing cell lines.

FIG. 2 is a graph showing typical time courses of biomass density in cultures of various inoculum densities.

FIG. 6 is a series of chromatographs for procyanidins and alkaloids from *Theobroma cacao* cell cultures. FIGS. 6D-6F show an HPLC LC-MS analysis of *Theobroma cacao* suspension cells.

FIG. 8 is a series of HPLC chromatograms of unfermented cocoa extract (FIG. 8A) and suspension cell extract (FIG. 8B) in fluorescence detector mode. The labels 1 through 12 indicate the degree of polymerization of procyanidins, respectively: 1, monomers; 2, dimers; 3, trimers; 4, tetramers; 5, pentamers; 6, hexamers; 7, heptamers; 8, octamers; 9, nonamers; 10, decamers; 11, undecamers; 12, dodecamers.

FIG. 9 is a series of HPLC chromatograms of unfermented cocoa extract (FIG. 9A) and suspension cell extract (FIG. 9B) in PDA detector mode at 280 nm.

FIG. 10 is a series of graphs showing procyanidin productivity and yield and carbohydrate consumption in *Theobroma cacao* cell cultures. FIG. 10A and FIG. 10B demonstrate procyanidin productivity (FIG. 10B) and production yield (FIG. 10A) of suspension cultures from non-floral and floral tissue.

DETAILED DESCRIPTION

I. Abbreviations

Figure 3:
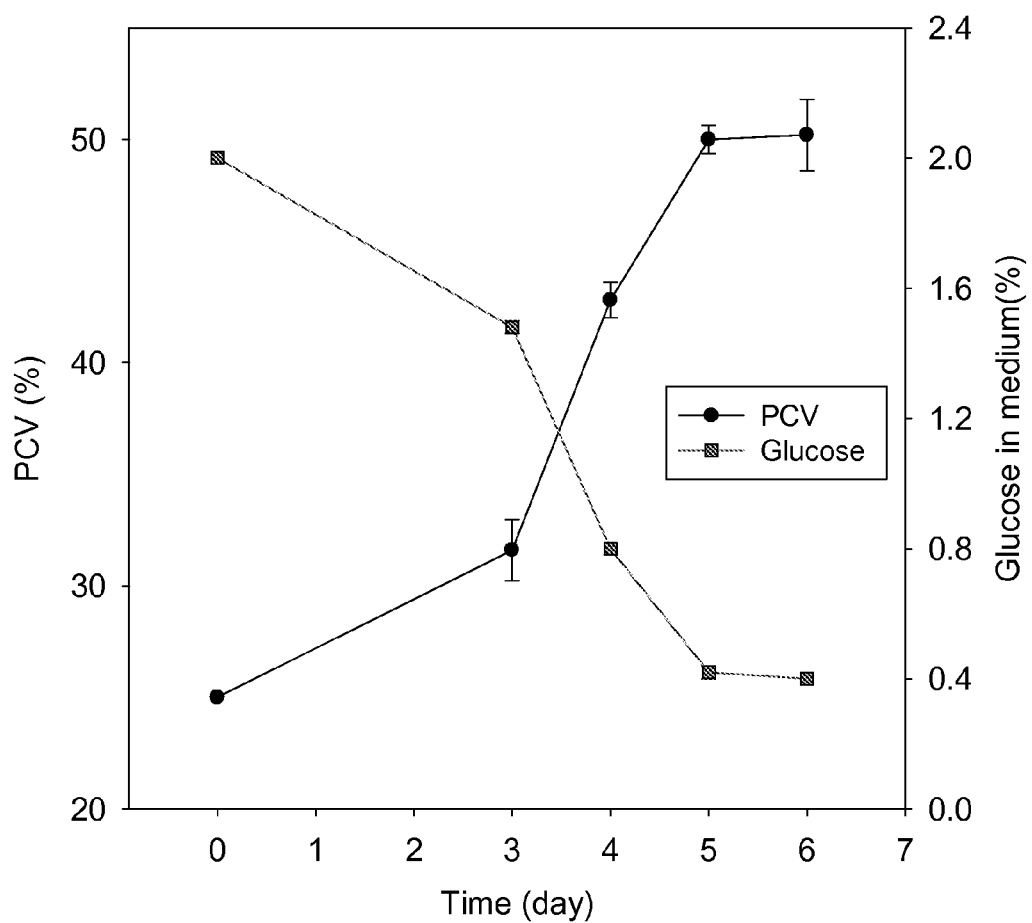
FIG. 3 is a graph showing cell growth and carbohydrate consumption over time of selected fine cells derived from vegetative tissue.

| | |
|---|---|
| 2,4-D | 2,4-dichlorophenoxyacetic acid |
| 2iP | 6-(γ,γ-dimethylallylamine) purine |
| B5 | Gamborg's B5 |
| BA | Benzyl adenine |
| CP | Chee and Poole |
| DKW | Driver and Kuniyuki Walnut |
| FAB/MS | Fast atom bombardment/mass spectrometry |
| HCl | hydrochloric acid |
| HPLC | High performance liquid chromatography |
| $H_2SO_4$ | Sulfuric acid |
| IAA | Indole acetic acid |
| IBA | Indole butyric acid |
| LC | Liquid chromatography |
| LSIMS | Liquid secondary ion mass spectrometry |
| MS | Mass spectroscopy |
| MS medium, vitamins, or Salts | Murashige and Skoog medium, Murashige and Skoog vitamins, or Murashige and Skoog Salts |
| NAA | 1-Naphthalene acetic acid |
| NMR | Nuclear magnetic resonance |
| NN | Nitsch and Nitsch |
| PCV | Packed cell volume |
| PDA | Photodiode array |
| QL | Quiorin and Lepoivre |
| RI | Refractive index |
| rpm | revolutions per minute |
| SH | Schenk and Hildebrandt |
| TDZ | thisdiazuron |
| TLC | thin layer chromatography |
| vvm | volume of gas per volume of culture per minute |
| WPM | McCown's Woody Plant Medium |

II. Terms

Unless otherwise noted, technical terms are used according to conventional usage. In order to facilitate review of the various embodiments of the invention, the following explanations of specific terms are provided:

Antioxidants are substances that reduce oxidative damage (damage due to oxygen) such as that caused by free radicals.

Callus is a mass of thin-walled, undifferentiated plant cells, developed as the result of wounding or culture on nutrient media.

Catechins are polyphenolic compounds which occur in plants naturally. They are also called flavan-3-ols.

Cocoa is the seed from *Theobroma cacao* (of the order Sterculiacae) and consists of mainly two varieties: Criollo and Forestero divided into several subvarities. A third group called Trinitario is a cross between Criollo and Forestero. Other species included here are, for example, *Theobroma grandiflorum, Theobroma obovatum, Theobroma speciosum, Theobroma subincanum* and *Theobroma sylvestris*.

Flavonoids are any of a group of compounds containing a characteristic aromatic trimeric heterocyclic nucleus, usually occurring in glycosidic form and widely distributed in plants, often as a pigment.

Polyphenols are water-soluble plant pigments that are also know as bioflavonoids, which encompass more than 4,000 chemically unique flavonoids that can be categorized according to their chemical structure. Polyphenol monomers include catechin, epicatechin, leucocyanidin. Polyphenol oligomers include procyanidins.

Procyanidins are polymeric compounds consisting of coupled catechin units ranging from two and greater than fifty units. Procyanidins are also commonly called proanthocyanidins or condensed tannins.

Suspension culture is the process by which either prokaryotic or eukaryotic cells are grown under controlled conditions in a liquid nutrient medium.

Tissue culture is the technique or process of keeping tissue alive and growing in a culture medium.

Xanthines, derivatives of xanthine (3,7-dihydro-purine-2, 6-dione), are a group of alkaloids that are commonly used for their effects as mild stimulants and as bronchodilators. Methylated xanthine derivatives include caffeine, paraxanthine, theophylline, and theobromine (found mainly in chocolate). These compounds inhibit phosphodiesterase and antagonize adenosine.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein in a first embodiment is a method of preparing a substantially xanthine alkaloid-free cocoa polyphenol preparation, which method comprises growing *Theobroma* or *Herrania* cells in suspension culture for a time sufficient and under conditions sufficient to result in production of cocoa polyphenols, and harvesting cocoa polyphenols from the cell suspension culture. In examples of this method, the resultant cocoa polyphenol preparation is substantially (or in some cases, completely) free of detectable caffeine and/or theobromine. In other specific examples, the preparation contains less than 50% of the levels of caffeine and/or theobromine as would be present in a cocoa polyphenol preparation made from fermented pods. In preferred embodiments, the cell-culture generated preparation contains less than 30%, less than 20%, less than 15%, less than 10%, or less than 5% of the levels of caffeine and/or theobromine as would be present in a cocoa polyphenol preparation made from fermented beans. In particular embodiments of the disclosed methods, *Theobroma* or *Herrania* cells are grown in suspension culture for a time sufficient and under conditions sufficient to result in production of cocoa procyanidins (for example, oligomeric procyanidins), and harvesting cocoa procyanidins from the cell suspension culture.

In representative methods provided herein, the *Theobroma* or *Herrania* cell suspension culture is produced by growing callus from an immature *Theobroma* or *Herrania* floral explant or from *Theobroma* or *Herrania* vegetative material on solid growth medium, selecting a rapidly growing cell line from the *Theobroma* or *Herrania* callus culture, and initiating the cell suspension culture by inoculating the rapidly growing cell line into liquid medium.

The production of cocoa polyphenols (including procyanidins) in certain of the provided methods comprises harvesting the cells; homogenizing cell biomass in a suitable solvent for extraction of polyphenol rich fraction; isolating a procyanidin rich fraction (e.g., using solvent-solvent extraction and/or chromatography); and optionally drying or concentrating the procyanidin fraction. Harvesting the cells in some cases comprises centrifugation, filtration, or a combination thereof.

Also provided is a substantially xanthine alkaloid-free cocoa polyphenol preparation produced using any one of the methods described herein. By way of example, a cocoa polyphenol preparation is considered substantially xanthine alkaloid-free if it contains less than 2% theobromine and less than 0.5% caffeine. In specific, non-limiting examples, a cocoa polyphenol preparation is considered substantially xanthine alkaloid-free if it contains less than 1.5%, less than 1%, less than 0.5%, or 0% theobromine and/or contains less than 0.25%, less than 0.2%, less than 0.1% or 0% caffeine. In another example, a cocoa procyanidin preparation is considered substantially xanthine alkaloid-free if it contains less than 2% theobromine and less than 0.5% caffeine. In specific, non-limiting examples, a cocoa polyphenol preparation is considered substantially xanthine alkaloid-free if it contains less than 1.5%, less than 1%, less than 0.5%, or 0% theobromine and/or contains less than 0.25%, less than 0.2%, less than 0.1% or 0% caffeine. The most desired substantially xanthine alkaloid-free level is 0% theobromine and 0% caffeine (the preparation is xanthine alkaloid-free).

Yet another embodiment is a method of producing a cell suspension culture of cacao cells. Examples of this method include growing callus from an immature *Theobroma* or *Herrania* floral explant or from *Theobroma* or *Herrania* vegetative material on solid growth medium; selecting a rapidly growing cell line from the *Theobroma* or *Herrania* callus culture; and initiating the cell suspension culture by inoculating the rapidly growing cell line into liquid medium. By way of example, the immature *Theobroma cacao* or *Herrania* floral explant is in some cases selected from staminode, sepal and petal base explants. In other specific, non-limiting examples, the *Theobroma cacao* or *Herrania* vegetative material is selected from young or mature leaves, stem, meristem, nodes, or internodes.

Optionally, the method of producing a cell suspension culture of cacao cells further comprises growing the cell suspension culture in flasks, any suitable culture vessels, or bioreactors. For instance, the growing in some cases is effected in vessels or bioreactors and in batch, fedbatch or continuous mode.

Also contemplated herein are *Theobroma* or *Herrania* cell suspension cultures produced by any one of the described methods, as well as use of these cell suspension cultures to produce cocoa polyphenols or, more specifically, procyanidins.

Another embodiment provided by this enclosure is a cocoa polyphenol preparation comprising a mixture of cocoa polyphenols and naturally substantially free of caffeine and theobromine, which preparation is extracted from a *Theobroma* or *Herrania* cell suspension culture. By way of example, a cocoa polyphenol preparation is considered substantially free of caffeine and theobromine if it contains less than 2% theobromine and less than 0.5% caffeine. In specific, non-limiting examples, a cocoa polyphenol preparation is considered substantially xanthine alkaloid-free if it contains less than 1.5%, less than 1%, less than 0.5%, or 0% theobromine and/or contains less than 0.25%, less than 0.2%, less than 0.1% or 0% caffeine. The most desired substantially xanthine alkaloid-free level is 0% theobromine and 0% caffeine. The term "naturally" in reference to "naturally substantially free of caffeine and theobromine" indicates that the relative absence of caffeine and theobromine occurs not through a purification procedure, such as LH-20 size exclusion chromatography. In other embodiments, the addition of supplemental glucose to the suspension culture, at the end of the exponential growth stage, augments procyanidin production.

A further embodiment is a cocoa polyphenol preparation that is produced without a defatting step using a hexane or another organic solvent. Thus, there is contemplated herein the preparation of cocoa polyphenols (for example, procyanidins) that are produced (e.g., extracted) without the use of a hexane.

Also provided in a specific embodiment is a cocoa polyphenol preparation, wherein extraction from a *Theobroma* or *Herrania* cell suspension culture comprises harvesting the cells, homogenizing cell biomass in a suitable solvent for extraction of polyphenol rich fraction, isolating a procyanidin rich fraction (for instance, using solvent-solvent extraction and/or chromatography); and optionally drying, lyophilizing, or concentrating the procyanidin fraction. For instance, harvesting the cells may include centrifugation, filtration, or a combination thereof.

It is contemplated that the cocoa polyphenol preparations provided herein may be used in a dietary composition, and/or in a therapeutic composition, and/or in a veterinary composition, and/or in a cosmetic composition.

It is further contemplated that representative preparations described herein and/or produced using the methods described herein contain cocoa polyphenols that comprise catechin, epicatechin, and procyanidin oligomers. In specific examples, the oligomers are dimers through dodecamers. For instance, in some preparations the oligomers comprise dimers, trimers, tetramers, pentamers, hexamers, heptamers, octamers, nonamers, or mixtures of any two or more thereof.

Also contemplated are preparations wherein the cocoa polyphenols are cocoa procyanidins.

Cocoa polyphenol preparations as provided herein may be provided in liquid form, dry form, or lyophilized form.

IV. Cocoa Tissue Culture

Described herein are methods for efficiently isolating procyanidins from cell cultures of *Theobroma* or *Herrania*. Specifically, *Theobroma* or *Herrania* cell suspension cultures have been established that allow routine isolation of procyanidins that are similar to the procyanidins extracted from cocoa beans. Moreover, methods provided herein have resulted in production of prolific cell culture source of these procyanidins. Representative advantages of these methods include:

- Reliable and continuous source of biomass due to control of climatic conditions
- Rapid and efficient isolation procedures that minimizes degradation of procyanidins during the extraction process.
- Procyanidins isolated from cell culture are similar in composition to those isolated from cocoa beans
- Techniques useful to manipulate and optimize cell culture procyanidin productivity In general, described herein is the establishment of callus cultures from various tissues of *Theobroma* or *Herrania* plant. Established calli are used to raise suspension cultures using various types of cell culture media. When stable suspension cell cultures are established the cells are extracted and analyzed for procyanidin content by recognized spectrophotometric methods, while HPLC-MS methods are used for identifying individual procyanidins. From such analysis, suspension cultures capable of producing the desired procyanidins are selected for further optimization of productivity.

Generation of Cocoa Culture

The process of generating cocoa cultures is generally outlined here, and detailed exemplary protocols are described in the Examples. Briefly, although the specifics may be varied by those skilled in the art according to known variations, initiation of the procyanidin-producing cell cultures is achieved by establishing callus and suspension cultures from explants derived from any of various plant parts, for example, floral tissues such as petals, sepals, staminodes, etc., or non-floral vegetative tissues such as node, internode, young leaves, mature leaves, as described for somatic embryogenesis. The suspension cultures are maintained in fresh suspension culture medium by periodic transfer of a portion of the cultured cells to fresh medium. Transfer schedule and inoculum density is determined by cell growth performance and sugar consumption from the medium.

One embodiment provides a method for modifying the content of procyanidins which involves initiating the procyanidin-producing cultures under conditions sufficient to initiate such cultures and establishing a production medium sufficient to establish productive cell cultures, followed by scaling up of the productive cell cultures for an appropriate amount of time to isolate the procyanidins. Accordingly, altering the conditions required to initiate a culture or establish productive cultures results in modified content (amount) of procyanidins in such cultures. Physical aspects (e.g., light irradiance) and/or chemical aspects (e.g., media composition or chemical elicitors) of the plant cell culture microenvironment may be varied to achieve the desired modified content.

For instance, carbohydrate (e.g. sucrose or glucose) concentration may be increased in a suspension medium in order to increase the amount of procyanidins in the culture. Furthermore, nitrogen sources (e.g., ammonium nitrate) may be manipulated for production of secondary metabolites in plant cell cultures (see Neera et al., *Phytochemistry*. 31(12): 4143-4149, 1992). Therefore, decreasing the concentration of nitrogen sources in *Theobroma* or *Herrania* cell culture medium might be used to increase production of procyanidins in the culture. In addition, infusion of certain amino acids (such as glutamine, glycine, and serine) also may significantly affect the production of secondary metabolites. As a result, the concentrations of these amino acids in *Theobroma* or *Herrania* suspension medium may be increased in order to enhance the production of procyanidins. Additional amino acids may also be included in the medium and tested for their ability to increase the production of procyanidins by suspension cultures of *Theobroma* or *Herrania*.

Lighting conditions also can be varied in order to achieve modified procyanidins content in cell cultures of *Theobroma* or *Herrania*. For example, the lighting can be changed by increasing irradiance or length of exposure to the light, thereby increasing procyanidin production. The wavelength of the light irradiance can also be changed to achieve increased production of procyanidins. For instance, UV light is known to induce anthocyanin production in plant cell cultures (Meyer, *J. Biotechnology* 93: 45-57, 2002).

Other modifications known in the art for manipulation of plant cell culture microenvironments are also contemplated as being within the scope of the present description and can be performed by anyone skilled in the art.

Harvesting of Cocoa Cells from Culture

A batch of cells of *Theobroma* or *Herrania* producing procyanidins are grown as described herein, and cells are harvested to extract the procyanidins. Harvesting of suspension cells can be performed in a number of ways, examples of which are described herein.

Once a cell culture has reached stationary phase and the desired productivity of procyanidins is reached, the culture is allowed to settle as a compact mass in the container and the medium can be decanted, leaving behind the mostly solid cell biomass. The cell biomass is then washed to remove remaining medium and similarly decanted. Alternatively, the cell suspension can be centrifuged and the supernatant (medium) discarded followed by washing of the cell mass and centrifugation again to discard the liquid. A third option is to filter the cell culture suspension to remove the medium. Any of these methods can be employed with cell culture volumes ranging from a few milliliters to production scale volumes of several thousand liters of cultures.

Extraction Procedures

The harvested cell mass is crushed, milled or ground to homogenize the cell mass and break up the cells to allow a better contact of extracting solvent with the sample, and to ensure that the extracted portion is representative for the entire sample.

Procyanidins are unstable compounds. Thus, if the cell biomass needs to be stored prior to extraction it is preferably stored frozen, for instance by freezing with liquid nitrogen.

Extraction of total polyphenols from cell cultures of *Theobroma* or *Herrania* is similar to procedures used for extracting total polyphenols from cocoa beans, except for a few major differences. In case of cocoa beans, the initial step after grinding the beans is to defat the ground flakes (nibs). This process results in a loss of polyphenols. Since cell cultures do not have as much fat as the beans, this step is not required. Removing this step reduces the loss of polyphenols during the extraction process from a cell culture.

Furthermore, defatting requires solvents such as hexane, and traces of the solvent are found in the final extract. This causes an unpleasant odor in extracts produced from cocoa beans, and the solvents may be toxic or undesirable for certain uses, such as a food ingredient. Since the methods described herein for extraction from cell culture biomass eliminate the use of solvents (such as hexane), there is no solvent contamination or unpleasant solvent odor in the resultant extract.

Polyphenols in a representative method are extracted from the ground, homogenized cells with 70-80% aqueous methanol or 70% aqueous acetone, or combinations thereof. Water and ethanol have also been used, though oligomeric procyanidins are extracted only partially using these solvents, and high molecular weight polymers are not extracted at all (Grayer, In J. B. Harborne, *Plant Phenolics* (Vol. 1), pp 283-323, 1989. San Diego, Academic Press, Inc.; Lee & Widmer, In L.M.L. Nollet, *Handbook of Food Analysis* (Vol. 1), pp 821-894, 1996, Basel, New York, Hong Kong, Marcel Dekker, Inc.).

After an exhaustive extraction for minor components, individual procyanidins may be present in the extract in a dilute level. Concentration is achieved at low temperature (below 40° C.) and under reduced pressure to minimize degradation of procyanidins (Lee & Widmer. In L.M.L. Nollet, *Handbook of Food Analysis* (Vol. 1), pp 821-894, 1996, Basel, New York, Hong Kong, Marcel Dekker, Inc.).

The polyphenol extracts from cell cultures of *Theobroma* or *Herrania* at this stage are relatively clean can be analyzed immediately. One benefit of the methods described herein is that cell culture-derived extracts of *Theobroma* or *Herrania* polyphenols have undetectable levels of impurities (e.g., caffeine and theobromine) to start with, compared to polyphenol extracts of beans. However, it may be beneficial to do further clean-up to remove minor impurities, such as caffeine and theobromine. It is possible to clean up the extract to remove even traces of these impurities. Such clean-up steps can include liquid-liquid partitioning with a non-miscible solvent and column chromatography on Sephadex LH-20, polyamide, Amberlite XAD-2, preparative HPLC, and solid phase extraction (SPE) using commercially available disposable cartridges (Grayer, In J. B. Harborne, *Plant Phenolics* (Vol. 1), pp 283-323, 1989. San Diego, Academic Press, Inc.; Markham & Bloor, In C.A. Rice-Evans and L. Packer, *Flavonoids in Health and Disease*, pp 1-33, 1998, Basel, New York, Hong Kong, Marcel Dekker, Inc.). Removal of theobromine and caffeine usually can be accomplished by extraction with chloroform or methylene chloride, since most flavonoids have limited solubility in these solvents.

Analysis Procedures

Analytical techniques used for detection and identification of procyanidins from *Theobroma* or *Herrania* cell cultures are similar to those used for extracts from beans. Identification of cocoa procyanidins has predominantly been achieved using a variety of chromatographic techniques for separation of oligomers and then using independent methods for structural characterization. Quesnel (*Phytochemistry* 7: 1583-1592, 1968) and Jalal and Collin (*Phytochem.* 16: 1377-1380, 1977) identified procyanidins in cocoa using paper chromatography and TLC methods, respectively. However, although these publications acknowledged the presence of procyanidins in cocoa, the stereospecific structures of the procyanidins were not elucidated. Porter et al. (*Phytochemistry* 30: 1657-1663, 1991) conducted a rigorous investigation of procyanidins in cocoa using column chromatography, TLC, HPLC, and negative ion FAB/MS to establish the presence of procyanidin oligomers through heptamers. Additionally they confirmed the structures of procyanidins through tetramers using NMR, and found them to consist primarily of (−)-epicatechin. Evidence of cocoa procyanidin oligomers through octamers was reported by Clapperton et al. (*Proceedings, 16$^{th}$ International Conference of Groupe Polyphenols*, Lisbon, Portugal; Groupe Polyphenols: Norbonne, France, Vol II, pp 112-115, 1992), who used a combination of column chromatography, reversed phase HPLC, and positive ion LSIMS to characterize the procyanidin oligomers. This work demonstrated the utility of positive ion LSIMS and the use of sodium adducts as means of identifying larger procyanidin oligomers. Unfortunately, all of these methods are laborious, require lengthy preparation times to obtain structural information, and are not amenable to high throughput analysis and screening of large numbers of cell culture samples. Also, these methods are not suitable for small samples.

For the current disclosure, we developed a high throughput microscale method for the extraction of procyanidins from *Theobroma* or *Herrania* cell cultures, reverse phase HPLC methods for rapid separation of procyanidin monomers and oligomers, and mass spectroscopy (MS) methods for simultaneous identification of procyanidin oligomers based on their molecular characteristics.

Large-scale Process Optimization of *Theobroma* or *Herrania* Cell Culture

Large-scale plant cell culture is important technology in the development of a commercial process. This can be performed in large tanks similar to those used in microbial fermentation. Productivity enhancement in these tanks can be achieved by determining biomolecular factors based on cellular growth and production characteristics in the large scale process and by optimizing large-scale bioprocess variables that enhance procyanidin productivity. Biomolecular factors include medium components, elicitors and precursors in biosynthetic pathway. Prior to large-scale process, these factors should be tested in flask-scale process, since the goal of scale-up process is to reproduce on a large scale those conditions observed to be optimal on the smaller scale. However, conditions in large-scale bioreactor culture can be different than *Theobroma* or *Herrania* suspended cells in flask-scale culture. The macrokinetics of the culture are affected by changes in environmental conditions affecting the suspended cells caused by transport limitation. For instance, while parameters of growth kinetics are scale independent, the overall growth of a cell culture in a vessel is scale dependent because of the scale dependency on transport of gaseous and dissolved nutrients and metabolites (Dicosmo & Misawa, *Plant Cell Culture Secondary Metabolism*, pp 11-44, 1996. Boca Raton, Fla., CRC Press LLC). Therefore, in scale up of the bioreactor process for cocoa procyanidin production, a number of basic experiments were performed to yield essential data of growth rate, product formation rate, nutrient uptake rate and respiration rate.

In general, high productivity in plant cell cultures can be achieved by increasing the cell concentration and specific productivity. The maximum cell concentration is dependent on the nutrient supply, yield of biomass per substrate and water content. Based on the basic data, additional environmental factors are varied one by one or multiple factors can be varied at one time to increase biomass. Bioprocess variables such aeration rate, rheological properties of suspension cultures affect mass transfer and mixing in bioreactors and in turn, influence not only cell growth but also production of plant secondary metabolites. Therefore, two stage cultures may be considered, because most polyphenols are usually non-growth associated compounds. Because single stage process ideally limits the culture to a single growth rate and presumably a single developmental stage, this operation would be unsuited when several developmental stages are prerequisite for production of the non-growth associated compounds. The variables of aeration rate, agitation speed, other mixing-related variables and even medium composition are optimized separately for growth stage and production stage. However, it is impossible to scale up a process while keeping all conditions optimal. A choice has to be made as to which variable is considered the most important.

The effects of supplementing carbon and nitrogen sources on growth and production are also studied based on basic engineering data of carbon and nitrogen consumption, since the relative amounts of carbon and nitrogen sources play an important role in enhancing the biosynthesis of secondary metabolites and cell growth (Basaria, *Current Biology*, 2: 370-374, 1990). Then, supply of oxygen and carbon dioxide can be studied. In addition to oxygen, carbon dioxide has been reported to improve cell growth and secondary metabolite production in plant cell cultures (Thanh et al., *Biologia Plantarum*, 50: 752-754, 2006; Tate & Payne, *Plant Cell Reports*, 10: 22-25, 1991). Oxygen requirements of plant cells are relatively low in cell growth stage, but may significantly increase during metabolite synthesis. The level of these gases is controlled for their optimal utilization in reactor culture of *Theobroma* or *Herrania* cells. In large scale fermentation, it is impossible to introduce the same amounts of gas (air, oxygen etc.) as can be introduced on a laboratory scale. Therefore, the mass transfer coefficient constant should be maintained in order to make the superficial gas velocity constant during the bioreactor process.

The use of elicitors to stimulate metabolite formation and secretion is an important process strategy. It has been very useful to reduce the process time necessary to reach a high product concentration, e.g. volumetric productivity. Further, elicitation may result in the formation of novel compounds (Payne et al., *Plant Cell and Tissue Culture in Liquid Systems*, pp333-351, 1995, New York, John Wiley & Sons, Inc). Optimization of elicitation with several biotic/abiotic candidates is tested in large-scale reactor culture to optimize when they should be treated, what dosage can be the best, how long the cells should be exposed to them and when the cells should be harvested. Synergistic effect using multiple treatments of elicitors is also tested to enhance productivity, since each elicitor can induce different type of enzymes in biosynthetic pathway.

Reactor operation method depends on cellular dynamics for growth, production and their relationship. As described earlier, the target compounds in this study are non-growth associated, which means two-stage culture process must be considered. Therefore, fed-batch culture is a particularly attractive option when the production time is considerably longer than the time required to grow the biomass and in this case, larger steps in the volume of the succeeding bioreactors are possible, resulting in a smaller number of bioreactors in the biomass train.

V. Use and Administration of Procyanidins

Procyanidins generated by the methods disclosed herein can be administered to a subject for therapeutic, dietary, or cosmetic purposes. The subject can be a human or veterinary mammal, such as a monkey, a horse, a cow, a pig, a dog, a cat, a mouse or a rat.

With regard to therapeutic uses, the procyanidins can be used to treat or prevent several disorders or diseases, such as atherosclerosis, cardiovascular disease, cancer, blood pressure modulation and/or hypertension. For example, the procyanidins can be administered prophylactically to a subject at risk of developing a tumor, to a subject having a tumor, or to a subject previously treated for a tumor. Treatment of the tumor includes, but is not limited to, surgical removal of the tumor, chemotherapy, immunotherapy or radiation therapy. In other embodiments, the procyanidins generated by the methods disclosed herein are administered to the subject in combination with at least one additional agent either prior to, simultaneously with, or following treatment of a tumor. The additional agent can also be another agent described herein that inhibits or reduces tumor growth. Alternatively, the additional agent can be an agent that improves the subject's ability to inhibit tumor growth or an agent (such as an antibiotic) that helps the subject fight infection during the course of treatment for the tumor. For example, the additional agent can be an agent that stimulates the immune system, such as a cytokine.

Procyanidins generated by the methods provided herein can be administered to a subject at risk of developing any type of tumor or to a subject suffering from any type of tumor. The tumor can be a benign tumor or a malignant tumor. The tumor can include a carcinoma, a sarcoma, a leukemia, a lymphoma, or a tumor of the nervous system. In several specific, non-limiting embodiments, the tumor includes a breast tumor, a liver tumor, a pancreatic tumor, a gastrointestinal tumor, a colon tumor, a uterine tumor, a ovarian tumor, a cervical tumor, a testicular tumor, a prostate tumor, a brain tumor, a skin tumor, a melanoma, a retinal tumor, a lung tumor, a kidney tumor, a bone tumor, an osteosarcoma, a nasopharyngeal tumor, a thyroid tumor, a leukemia, or a lymphoma. In general, the procyanidins generated by the methods provided herein are administered to a subject in an amount sufficient to prevent or inhibit tumor growth.

In other embodiments, the procyanidins can be administered prophylactically to a subject at risk of developing atherosclerosis, cardiovascular disease, or hypertension. Alternatively, the procyanidins can be administered to a subject to treat an existing condition, such as atherosclerosis, cardiovascular disease, or hypertension. The compositions can be co-administered or sequentially administered with other agents, such as antineoplastic agents, antioxidants, or agents that alleviate the symptoms or conditions associated with atherosclerosis, cardiovascular disease, blood pressure modulation and/or hypertension.

In addition, the procyanidins generated by the methods disclosed herein can be used in dietary compositions. When orally administered in the form of a liquid, the liquid may be water-based, milk-based, tea-based, fruit juice-based, or some combination thereof. Solid and liquid formulations for internal administration can further comprise thickeners sweeteners.

The procyanidins generated by the methods disclosed herein can also be used in cosmetic compositions to improve the quality or appearance of the skin of a subject. Improved skin appearance, texture, and moisture can be achieved by administering the procyanidins composition externally, internally, or some combination thereof. An acceptable carrier may act variously as solvent, carrier, diluent or dispersant for the constituents of the composition, and allows for the uniform application of the constituents to the surface of the skin at an appropriate dilution. The acceptable carrier may also facilitate penetration of the composition into the skin.

Compositions containing the procyanidins generated by the disclosed methods are useful in a wide variety of finished products, including pharmaceutical products, food products, and beverage compositions and can be prepared in accordance with standard techniques well known to those skilled in the pharmaceutical arts. Pharmaceutical compositions that include an active agent can be formulated with an appropriate solid or liquid carrier, depending on the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the procyanidin composition to be administered can also contain minor amounts of non-toxic auxiliary substances, such as wetting or emulsifying agents, preservatives, and pH buffering agents and the like, for example sodium acetate or sorbitan monolaurate.

In addition to injectable fluids, topical and oral formulations can be employed. Oral formulations can be liquid (for example, syrups, beverages, solutions, or suspensions), or solid (for example, powders, pills, tablets, or capsules). For solid compositions, conventional non-toxic solid carriers can include pharmaceutical grades of mannitol, lactose, starch, or magnesium stearate. Topical preparations can include eye drops, ointments, creams, sprays and the like. Preferably, formulations of the present invention that are suitable for topical administration are mixed with a solvent, carrier, diluent or dispersant for the constituents of the composition, and allows for the uniform application of the constituents to the surface of the skin at an appropriate dilution. The acceptable carrier may also facilitate penetration of the composition into the skin.

The dosage form of the procyanidin composition will be determined by the mode of administration chosen. Actual methods of preparing such dosage forms are known, or will be apparent, to those skilled in the art.

The procyanidin compositions generated by the methods of this disclosure can be administered to humans or veterinary mammals on whose cells they are effective in various manners such as topically, orally, intravenously, intramuscularly, intraperitoneally, intranasally, intradermally, intrathecally, and subcutaneously. The particular mode of administration and the dosage regimen will be selected by one skilled in the art, taking into account the particulars of the case (for example, the subject, the disease, the disease state involved, and whether the treatment is prophylactic). Treatment can involve daily or multi-daily doses of compound(s) over a period of a few days to months, or even years.

Such compositions can be administered to a subject in need of such administration in dosages and by techniques well known to those skilled in the medical, nutritional, or veterinary arts taking into consideration such factors as the age, sex, weight, and condition of the particular subject and the route of administration.

Preparation, dosage, and administration of compositions for therapeutic, dietary, cosmetic, and veterinary use are well known in the art (see, for example, U.S. Pat. Nos. 5,554,645, 5,853,728, 6,194,020, 6,312,753, 6,998,417, 7,122,574, 7,314,634, 7,320,797 and U.S. Patent Application Publication No. 2007/0148107, all of which are incorporated herein by reference).

The following examples are provided to illustrate certain particular features and/or embodiments. These examples should not be construed to limit the invention to the particular features or embodiments described.

EXAMPLES

Example 1

*Theobroma cacao* Callus Induction and Proliferation from Floral Tissue

Compact callus aggregates were established using full strength Driver and Kuniyuki walnut (DKW) medium augmented with auxin (2 mg/L 2,4-dichlorophenoxyacetic acid (2,4-D)), cytokinin (0.005 mg/L thisdiazuron (TDZ)) and the other supplements (250 mg/L L-glutamine, 100 mg/L myo-inositol) under controlled conditions using [$D^+$]-glucose as the carbon source (Medium I in Table 1). The medium was sterilized by autoclaving after adjusting the pH to 5.8. Samples of *Theobroma cacao* immature flower materials were collected from a number of cultivated plants. To prevent contamination of the culture, the materials were surface-sterilized prior to introducing them to the culture medium. The material was first immersed in 1% (w/v) sodium hypochlorite for 20 minutes and gently agitated every 5 minutes. Under sterile conditions the material was decanted and rinsed three times with sterile deionized water and gently agitated during each rinse. The final rinse was decanted and only the flower buds were transferred to sterile Petri plates. The flower buds were cut across at a position ⅓ of the flower length from the base using a sterile scalpel. Staminodes, sepal and petal base explants were extracted through the opening at the cut end.

The extracted materials were plated on solid callus induction medium. About 50 explants were distributed on the entire surface across each plate. The Petri plates were sealed with parafilm and maintained in the dark at 25° C. for 14 days. Substantial callus formation was observed after 10 days. Within 14 days of placing the flower parts on callus inducing medium, the callus was separated from the explants and placed on the callus proliferation media of Medium I, II and III listed in Table 1. At four week intervals, rapidly growing cells were isolated from the surface of the callus and subcultured to fresh medium. Rapidly growing cell lines showing a whitish to pale yellow color were selected for subculture (FIG. 1).

Example 2

*Theobroma cacao* Callus Induction and Proliferation from Vegetative Tissue

Callus was established on Murashige and Skoog (MS) medium, supplemented with auxins (2 mg/L IAA and 4 mg/L IBA), cytokinins (0.005 mg/L TDZ), and L-Glutamine (250 mg/L) with Glucose (20 g/L) as the carbon source (Medium XXVII, Table 1). The medium was sterilized by autoclaving, after adjusting the pH to 5.8. Samples of *Theobroma cacao* vegetative material (young and mature leaves, nodes and internodes) was collected from a number of greenhouse grown plants. To prevent contamination of the culture, the materials were surface-sterilized prior to introducing them to the culture medium. The material was first immersed in 70% ethanol for 1 minute, followed by immersion in 25% bleach for 10 minutes and gently agitated every 5 minutes. Under sterile conditions the material was decanted and rinsed three times with sterile deionized water and gently agitated during each rinse. Leaves were cut into 5 mm squares and nodes and internodes into 1-2 mm cylinders, and explanted onto plates containing solid medium. Plates were maintained in the dark at 25° C. They were observed everyday for signs of contamination and the contaminated material was discarded. Callus formation was observed after 4 weeks. After 6 weeks, the callus was separated from the explants and placed on the callus proliferation media as described above and as shown in Medium XXVII (Table 1). However, after initiation, the callus proliferated and established very rapidly. Newly formed cells were isolated from the surface of the callus and subcultured to fresh medium at two week intervals. Rapidly growing cell lines showing a pale yellow to light brown color were selected for subculture.

After establishing the cocoa callus, it was necessary to test the effect of lower amounts of auxin on the sustainability of the callus because the high auxin content in medium XXVII was retarding cell growth and formed very brown callus in subsequent generations, indicating that the cells were experiencing stress. Various media were tested for their ability to sustain the cocoa callus as well as the downstream effect of the maintenance medium on cell suspension creation. Medium XXVII had 6 mg/L of auxins (2 mg/L IAA and 4 mg/L IBA), 2X MS vitamins and 250 mg/L of glutamine supplemented on to MS medium with 20 g/L of glucose and 7 g/L agar. For maintenance, the auxin in the medium was reduced to 4 mg/L (2 mg/L IAA and 2 mg/L IBA, medium XXVIII in Table 1) and 2 mg/L auxin in the form of IBA (medium XXIX in Table 1).

Reducing the auxin to 4 mg/L improved the color of the callus from dark brown to light brown through yellow. The callus cell growth was back up to vigorous levels. Cell suspension cultures were established with the same ease as those established from healthy callus subcultured on medium XXVII.

In medium with 2 mg/L auxin the color of the callus changed and the cell growth was back up to vigorous levels. However, when these calli were subcultured onto the same medium, the cell growth of callus was reduced, compared to callus on medium XXVIII.

After reducing the auxin to 2 mg/L, the effect of removal of extra MS vitamins (Medium XXX in Table 1) in conjunction with removal of glutamine (Medium XXXI in Table 1) on growth was also recorded. Callus from these two media did not look different in growth characteristics from callus on medium XXIX. However, it was noticed that the presence of the extra vitamins in the medium was advantageous in terms of production of procyanidin. The best medium for maintaining the cocoa vegetative callus was medium XXVIII as this allowed for long term sustainability of callus as well as allowing easy establishment of cell suspension and maintenance of procyanidin productivity.

Example 3

*Theobroma grandiflorum* and *Theobroma obovatum* Callus Induction and Proliferation Callus cultures of *Theobroma grandiflorum* and *Theobroma obovatum* are established using methods such as those described in Examples 1 and 2 for *Theobroma cacao*.

Example 4

Suspension Initiation

Cell suspension cultures were established by inoculating white fresh calli raised from floral explants described in Example 1 into 125 ml Erlenmeyer flasks containing 25 ml of 20 different kinds of liquid media (Medium IV-XXIII; Table 1). The flasks were covered with silicone foam caps and agitated at 120 rpm with gyratory shaking in a thermostatically controlled room at 24±1° C. under complete darkness for 54 days. The subcultures were transferred weekly or biweekly as deemed necessary. Cultures that formed as either granular or fine suspension of cells were retained, while cultures that did not form suspension cultures were discarded. After 14 days of cell growth, 10% (v/v) of the cells were transferred into new 125 ml flasks containing 25 ml of fresh medium and were thereafter subcultured biweekly. Medium VIII showed the best performance (45% PCV at day 14) of cell propagation in suspended cell initiation.

For raising suspensions of non-floral (vegetative) tissue (node, internode, young leaves, mature leaves), calli generated in Example 2 were transferred to liquid medium in a manner similar to that described above for floral explants. The medium used was Medium XXIV, which differs from the regular maintenance Medium VIII in terms of the type of salts (MS salts, rather than DKW salts, which contain more ammonium and nitrogen source and lower sulfate), and includes 2 mg/L IAA and 4 mg/L IBA as auxins instead of 2,4-D (Table 1). In this medium, suspension cultures were established faster and the calli consumed all the sugar in the medium in seven days, whereas it takes usually 2 to 3 weeks for calli initiated in Medium VIII to consume the entire carbohydrate source. The procyanidin productivity of these established suspensions of non-floral tissue was also higher than that of the suspensions raised from floral tissue (1.1 g of total procyanidin/L of culture) (FIGS. 10A and 10B).

Example 5

Suspension Cell Growth

This example describes methods used to increase cell growth of suspensions.

Cell culture productivity increases as a function of the rate of cell growth and the density at which cell growth stops. To determine the optimal inoculation density, suspension cultures of *Theobroma cacao* cells were initiated with a starting cell density of 10, 15 and 20% (v/v) and allowed to grow for 14 days. FIG. 2 shows typical time courses of biomass density as a function of inoculum density. Cultures initiated at a cell density of 10% showed a significant lag in growth and did not reach maximal density within 14 days. Cultures initiated at a cell density of 15% and 20% in Medium VIII doubled in density within 13 days and reached a maximal average cell density of 40-43% within 14 days. However, some cultures showed over 50-60% packed cell volume (PCV) at day 14 after the cell selection process.

Medium VIII and Medium I are identical recipes except that Medium VIII does not contain Phytagel. Both these media are based on DKW salts and vitamins prepared using several stock solutions which could lead to batch to batch variation in media components. Thus, Medium XXXII was created using premixed DKW basal salts (Phytotechnology Laboratories, LLC, Catalogue #D190) and suspension cell growth was compared between media VIII and XXXII. There were no significant differences in growth of cells in either media. Thus, Medium XXXII was routinely used for the maintenance of suspension cultures.

Similar studies are performed with *Theobroma grandiflorum* and *Theobroma obovatum*. Cell culture productivity increases as function of the rate of cell growth and the density at which cell growth stops. To determine the optimal inoculation density, suspension cultures of *Theobroma grandiflorum* and *Theobroma obovatum* cells are initiated with a starting cell density of 10, 15 and 20% (v/v) and allowed to grow for 14 days.

In general, cultures initiated at a higher density have a shorter growth period or reach maximum cell density earlier. Cultures initiated at a cell density of 10% show a significant lag in growth and do not reach maximal densities within 14 days. Cultures initiated at a cell density of 15% and 20% double in density within 13 days and reach a maximal cell density of 40-43% within 14 days. This growth rate is slower than that reported previously for other plant cell suspension cultures, such as *Taxus* sp. However, cell growth of *Theobroma* cell cultures may be increased by further optimization of the growth medium and rigorous cell selection as described in Example 6, below.

Example 6

Cell Selection Process for Creating Homogeneous Cell Lines from Vegetative Cell Suspension Cultures Newly created cell suspension cultures are normally a heterogeneous mixture of cells. This heterogeneity results in unbalanced cell growth and unstable production pattern of desired metabolites in large-scale suspension cultures. Homogeneous cell cultures that are appropriate for large scale production can be derived from these heterogeneous mixtures by subculturing and selecting cultures with the desired characteristics. Selective and rapid screens were developed to detect polyphenols and cell growth to assist in this process. Butanol-HCl hydrolysis method, described in Example 8 was used to monitor polyphenol accumulation and Packed Cell Volume (PCV(%)=cell volume×100/total culture volume) was employed as a measure of biomass. The rate of carbohydrate consumption was measured by refractive index (Brix %) as a measure of cellular metabolism.

Vegetative tissue (nodes) derived suspension cultures were derived from calli as described in Examples 2 and 4. One well-growing cell line (MX1440-3496) was selected and grown in three different media that varied in the type of basal media (DKW salts versus MS medium) and types and amounts of hormones (Media XXXII, XXXIII and XXXIV in Table 1). Packed Cell Volume (PCV) in Media XXXII and XXXIV was just 33.7±4.7% and 25.7±4.0% on day 7, which showed slower growth than Medium XXXIII (47.6±6.6%). Cell growth rate is significantly important for maximizing the volumetric productivity in cell culture process. Medium XXXIII was also superior in carbohydrate consumption rate measured by refractive index (RI) of spent medium. Thus, it was chosen as maintenance medium for the further cell selection process of MX1440-3496 cell line.

Figure 4:
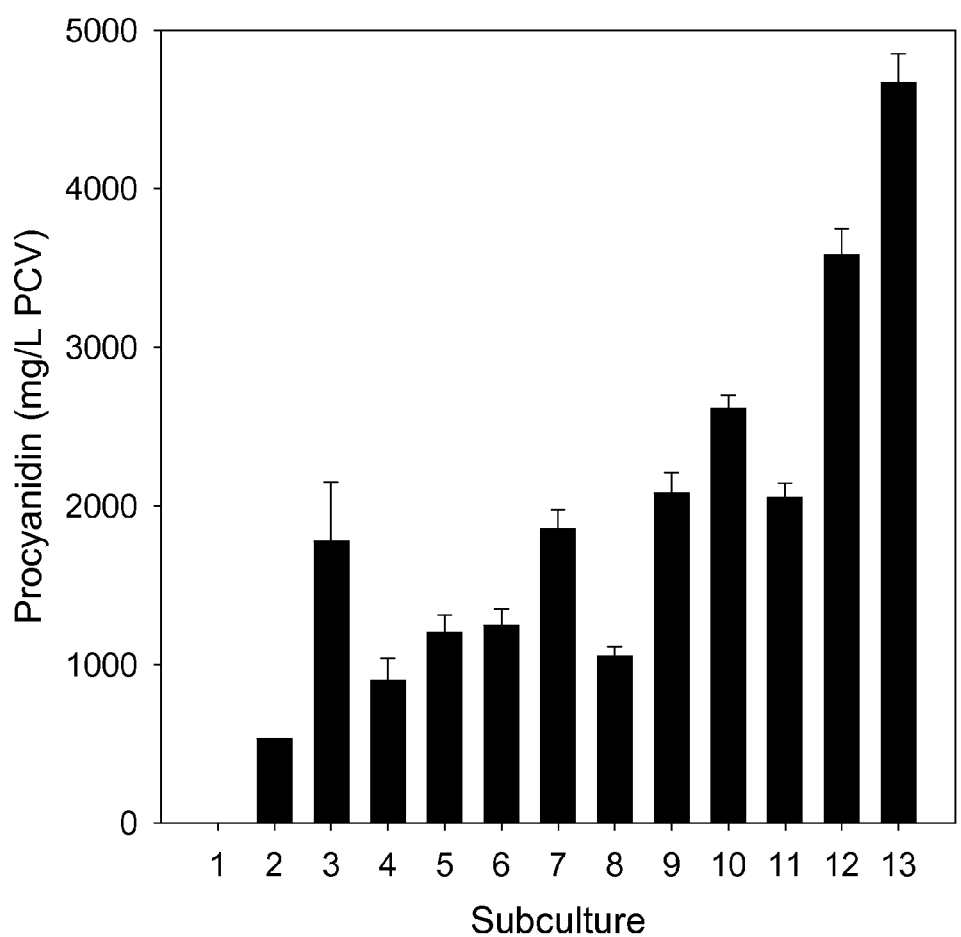
FIG. 4 is a graph showing procyanidin production improvement over time due to cell selection process of cells derived from vegetative tissue.

Well-growing, fine cells that are not clumpy or forming aggregates were preferably selected at each subculture time to increase the volumetric productivity and eliminate aggregated cells, since selection of large or clumpy cell aggregates leads to poor culture performance. Therefore, the selected cells had mainly yellow-colored fine cell morphology and the fine suspension culture resulted in better growth and production of homogeneous suspension culture. The MX1440-3496 cell line initially grew at a doubling time of over 10 days, while the doubling time showed a decrease to 5 days after executing the cell selection process (FIG. 3). Total procyanidin production level was initially 0.5 g/L PCV before the cell selection process, but increased by 8.9 times (4.7 g/L PCV) with the cell selection process (FIG. 4).

Example 7

Extraction of Polyphenols from *Theobroma* Callus Culture and Suspension Cultures This example describes methods developed for extracting polyphenols from callus and suspension cells of *Theobroma* cultures developed in examples 1-4. Experiments in this example specifically used cultures of *Theobroma cacao*. Polyphenols were extracted from approximately 0.25±0.04 g fresh weight of calli with 1.5 ml 50% (v/v) ethanol including 0.1% $H_2SO_4$, and 0.1±0.003 g dried weight of suspended cells (no supernatant medium) with 1.5 ml 80% (v/v) methanol including 0.1% $H_2SO_4$. The cells were placed in a micro-centrifuge tube (2.0 ml) and homogenized with a bead mill homogenizer for 1 minute. The homogenates were centrifuged at 3500 rpm for 20 minutes and only the supernatants were moved to another micro-centrifuge tube.

When large numbers of suspended cell cultures needed to be screened, a more robust high throughput method was used as follows: From each flask of cell culture to be analyzed, 1 ml was aliquoted into a 96-deep well plate. The packed cell volume (PCV) of the sample was also recorded prior to transfer to the 96-deep well plate. Cells in each well were pelleted by centrifuging the plate at 6000 rpm for 4 minutes in a bench top centrifuge. The supernatant from each well was removed and discarded with a plastic transfer pipette. Next, 0.5 ml of extraction solvent (80:20 methanol:water) and a tungsten carbide bead were added to each well, and the plate was placed on a Mixer Mill to grind the cells at 15 Hz for 2 minutes. The plate was then transferred to the centrifuge and cell debris was pelleted by centrifugation at 6000 rpm for 4 minutes.

Example 8

Preliminary Analysis of Polyphenol Production in Culture

The method used to carry out the procyanidin analysis reaction was designed to approximate fairly closely the original Swain and Hillis (*J. SCI. Food Agric.* 10:63, 1959) method and Porter et al. (*Phytochemistry*, 25(1):223, 1986) method. The butanol-HCl extraction assay was used to measure polyphenols in the extracts of *Theobroma cacao* suspended cells. The polyphenols are hydrolyzed to the monomers of (−)-epicatechin and cyanidin by combining 0.1 ml of aqueous methanol extract and 1.0 ml of butanol-HCl reagent (95:5 v/v) and heating the solution at 75° C. for 60 minutes in a Qiagen deep well block (Valencia, Calif., USA). Presence of cyanidin in the hydrolyzed sample was observed by the formation of a pink color. The absorbance at 280 and 520 nm was determined, and procyanidin content was calculated based on the amount of cyanidin formed using a calibration curve created using different concentrations of procyanidin B2 purchased from Chromadex, Inc. (Irvine, Calif.). Brighter pink color indicated higher concentration of procyanidins in suspension cultures (FIG. 5). Based on this method the procyanidin content of several suspension cultures ranged from 250 mg/L to 1000 mg/L.

Example 9

Analysis of Polyphenols from *Theobroma cacao* Cells

Figure 6A:
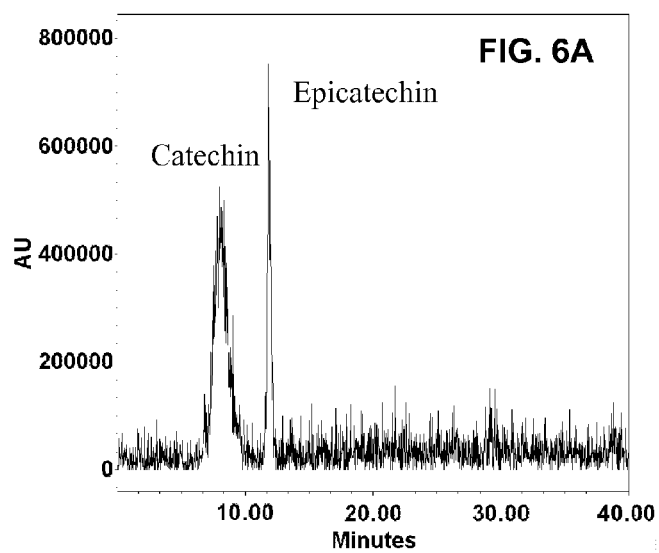
FIGS. 6A-6C that represent HPLC LC-MS analysis of various authentic standard compounds.
Figure 6B:
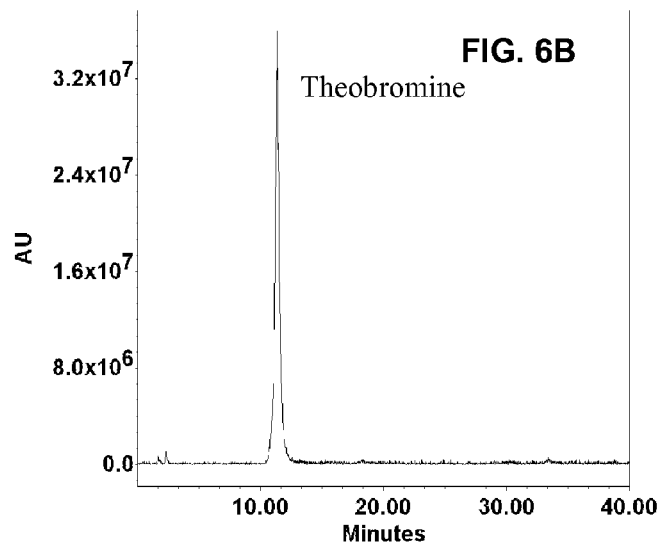
Figure 6C:
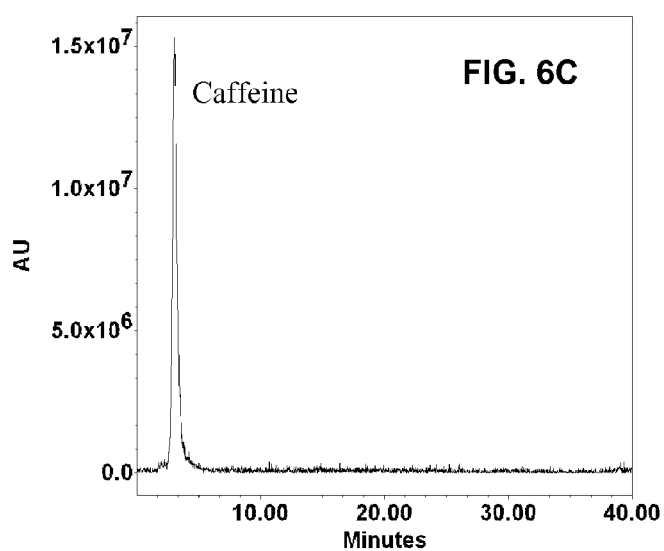

The aqueous methanol extract from Example 7 was filtered through 0.45 μM Millipore filters and 100 μl of the sample was injected to LC-MS analysis. A Symmetry C18 column (100×2.1 mm i.d., 3.5 μm) (Phenomenex, Torrance, Calif., USA) was used. LC analyses were performed using a Waters (Milford, Mass., USA) Alliance HPLC system equipped with a CTC Analytics PAL autosampler (Leap Technologies, Carrboro, N.C., USA), Waters 626 pump with 600S Controller and a Waters 2996 photodiode-array detector (PDA) scanning from 190 to 780 nm. MassLinx™ was used for data analysis. Gradient elution was carried out with water-0.1% formic acid (solvent A) and acetonitrile-0.1% formic acid (solvent B) at a constant flow-rate of 0.3 ml min$^{-1}$. A linear gradient profile with the following proportions (v/v) of solvent B was applied (t(min), % B): (0, 7), (5, 15), (20, 75), (25, 100), (35, 100), (35.1, 7) (45, 7). The compounds of (+)-catechin, (−)-epicatechin, caffeine, theobromine and procyanidins (dimer to hexamer) were monitored at 280 nm. A Waters Quattro Micro triple-quadrupole mass detector (Milford, Mass., USA) was used to obtain the MS data. Full-scan data acquisition was performed, scanning from m/z 150 to 1200 in profile mode for callus and from m/z 150 to 1800 for suspended cells. Authentic standards for catechin, epicatechin, theobromine and caffeine were purchased from Chromadex. Inc (Irvine, Calif.) and appropriate dilutions of each in aqueous methanol were also subjected to the same LC-MS analysis as the extracts from suspension cells (FIGS. 6A to 6C).

The levels of theobromine and caffeine, the major alkaloids in individual defatted *Theobroma cacao* seeds, were determined to be 25.2 mg/g dry weight and 4.6 mg/g dry weight, respectively. In contrast, *Theobroma cacao* suspended cells did not produce measurable caffeine or theobromine (FIGS. 6E and 6F) while they produced catechin and epicatechin at levels comparable to the seeds (FIG. 6D). These results demonstrate that plant cell cultures can produce high concentrations of the compound of interest with little contamination by unwanted compounds Example 10

Figure 10C:
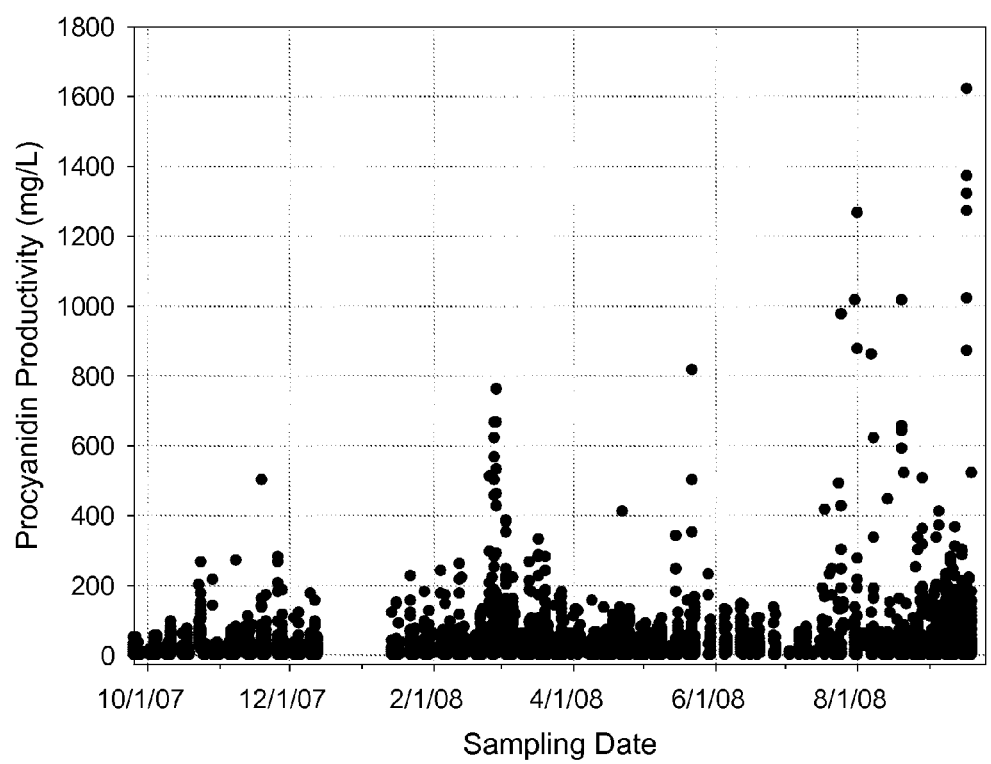
FIG. 10C. shows the cell selection effect on procyanidin productivity improvement.
Figure 10D:
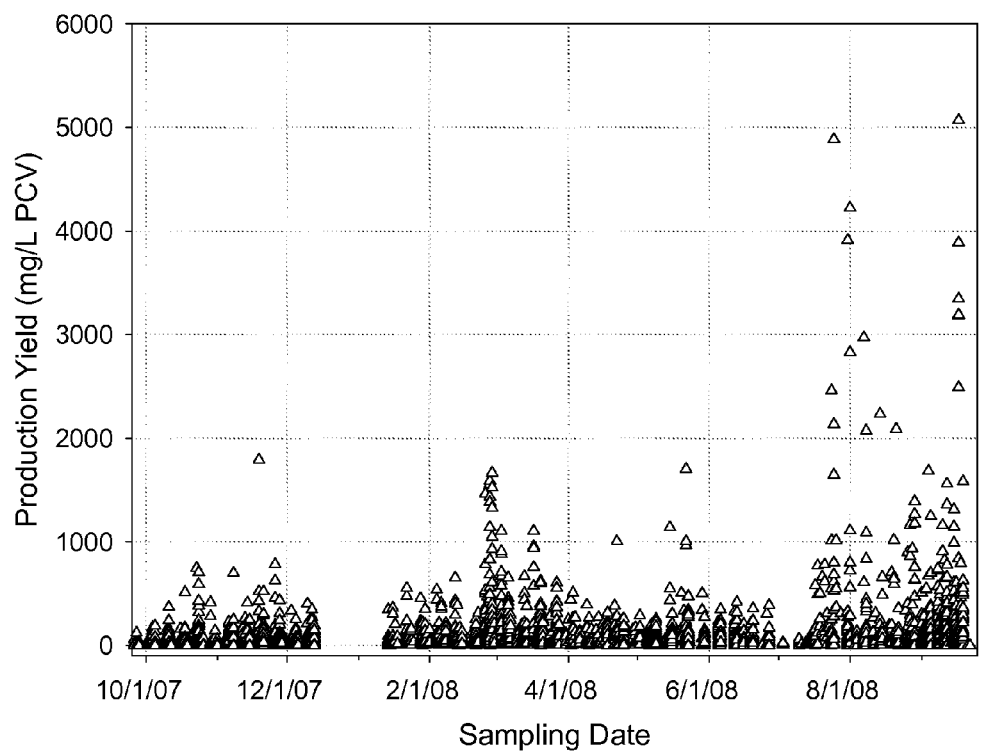
FIG. 10D shows the cell selection effect on procyanidin production yield improvement.

Cell Selection and Medium Optimization Process for Floral Derived Cell Suspensions Biomass increase, sugar consumption, and procyanidin productivity were measured every seven days of culture. These data are very important for desirable cell selection process. Well-growing cells were preferentially selected based on PCV and sugar consumption measurements, and well-producing cell lines were then chosen among the well-growing cell lines based on procyanidin production yield. Higher biomass and higher procyanidin production yield can increase productivity in a batch cycle. Average procyanidin productivity before the cell selection process was 52 mg of procyanidin/L of culture, which improved up to the level of 251 mg/L after one year of the cell selection process, and the highest level achieved was 1600 mg of procyanidin per liter of culture (FIG. 10C). The highest production yield increased to over 5000 mg/L of PCV as well (FIG. 10D).

Medium XXV was developed using B5 major salts and MS minor salts, thus lowering the concentration of ammonium ions in the medium compared to the usual maintenance medium of Medium VIII. Carbohydrate source was 60 g/L sucrose and hormones were 0.1 mg/L NAA and 0.2 mg/L kinetin, compared to 2 mg/L 2,4-D and 0.005 mg/L TDZ. Over the course of 2 weeks, the suspension tested in Medium XXV showed no growth, but procyanidins accumulated in the suspension to levels 4 times greater than in the control Medium VIII (over 95 mg/L with Medium XXV, compared to 22 mg/L with Medium VIII). This could be due to the higher ratio of nitrate/ammonium ions in this medium, coupled with an excess of cytokinin, compared to auxin.

Figure 10E:
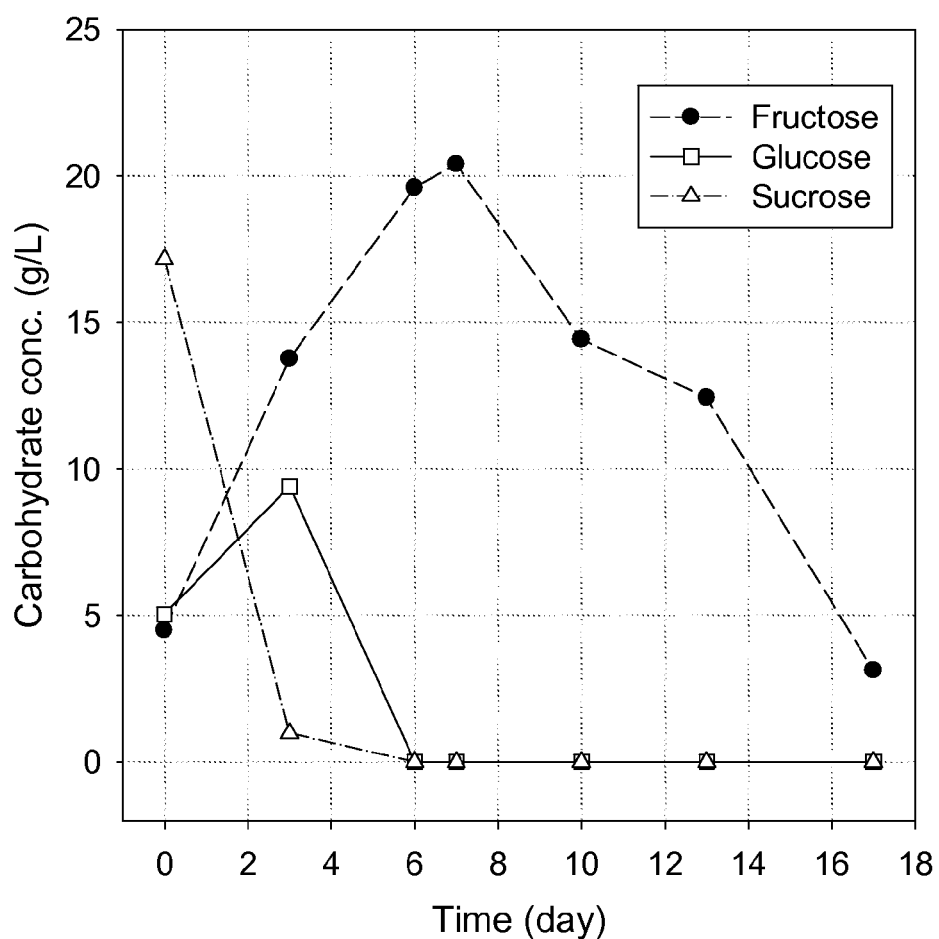
FIG. 10E shows carbohydrate analysis of *Theobroma cacao* cell culture in Medium XXVI (Table 1).

Medium XXVI was developed with MS salts, 30 g/L sucrose, and 2,4-D at 1.5 mg/L. Suspension cultures transferred in this medium showed a higher accumulation of procyanidin to levels 4 times greater at day 13 than in the control Medium VIII (87 mg/L of procyanidin with Medium XXVI, compared to 22 mg/L with Medium VIII). Whereas cell growth is relatively similar between the two media (61% PCV from 22% PCV in Medium VIII, compared to 60% PCV to 25% PCV in Medium XXVI), sugar consumption was different, indicating the cells would prefer glucose as carbohydrate source (FIG. 10E).

Example 11

Glucose Addition for Productivity Enhancement

This example describes the development of a protocol for increasing the procyanidin productivity of suspension cultures of cacao through supplemental addition of glucose.

Plant secondary metabolite production has been induced by changing medium from a growth medium to a production medium. For production medium optimization, either carbohydrate source or nitrogen source can be considered as critical factors. Additional carbohydrate in the form of glucose was used at the end of the exponential growth stage in order to enhance procyanidin production from floral and vegetative tissue-derived suspension cultures.

Significant improvements in procyanidin productivity were obtained from a floral tissue-derived suspension cell line (MX1241-58) by glucose addition. For 7 days, the culture was normally maintained in Medium XXXII under the normal culture condition as described in Example 5. MX1241-58 cell culture was sampled at day 7 before glucose addition and its PCV and RI were 49.5±3.5% and 0.2 on average. The average procyanidin production level was 189.5±17.7 mg/L PCV. At day 7, 5 ml of 50% glucose stock solution was added to the suspension culture to adjust RI to over 3% and was subsequently repeated when glucose concentration in medium was below 0.5%. After the glucose addition, the culture in the flask was shaken vigorously by hand for approximately 10 seconds to disperse the concentrated glucose in the suspension and the RI was measured again, which was 3 on average. With 3-4 times glucose addition at different culture days (at day 7, 11, 16 and 21) and one time fresh medium addition (day 25), procyanidin production level increased to up to 4.4 g/L PCV, which was 24 times higher than its initial value and PCV increased from 49.5±3.5% to 69.0±1.4%.

A similar treatment was applied to the cell line MX1440-3496 (described in Example 6) to improve its production level. This experiment was designed to test the cell line's response to glucose addition. MX1440-4496 cell line was maintained in Medium XXXIII, as described in Example 6. At day 6, 6 flasks of MX1440-3496 cell line were randomly chosen and divided into two sets of three flasks each. One set of three flasks were treated with a 50% glucose stock solution and the other 3 flasks were left untreated. The measurements prior to glucose addition for all six flasks on day 6 were, on average, 45% of PCV, 0.3±0.1 of RI and 2.41±0.19 g/L PCV of procyanidin production. 5 mL of 50% glucose stock solution was added to the three treated flasks. The average RI of the treated flasks after glucose addition increased to 6.0±1.1 and the average PCV was 39.7±0.6%.

Figure 7:
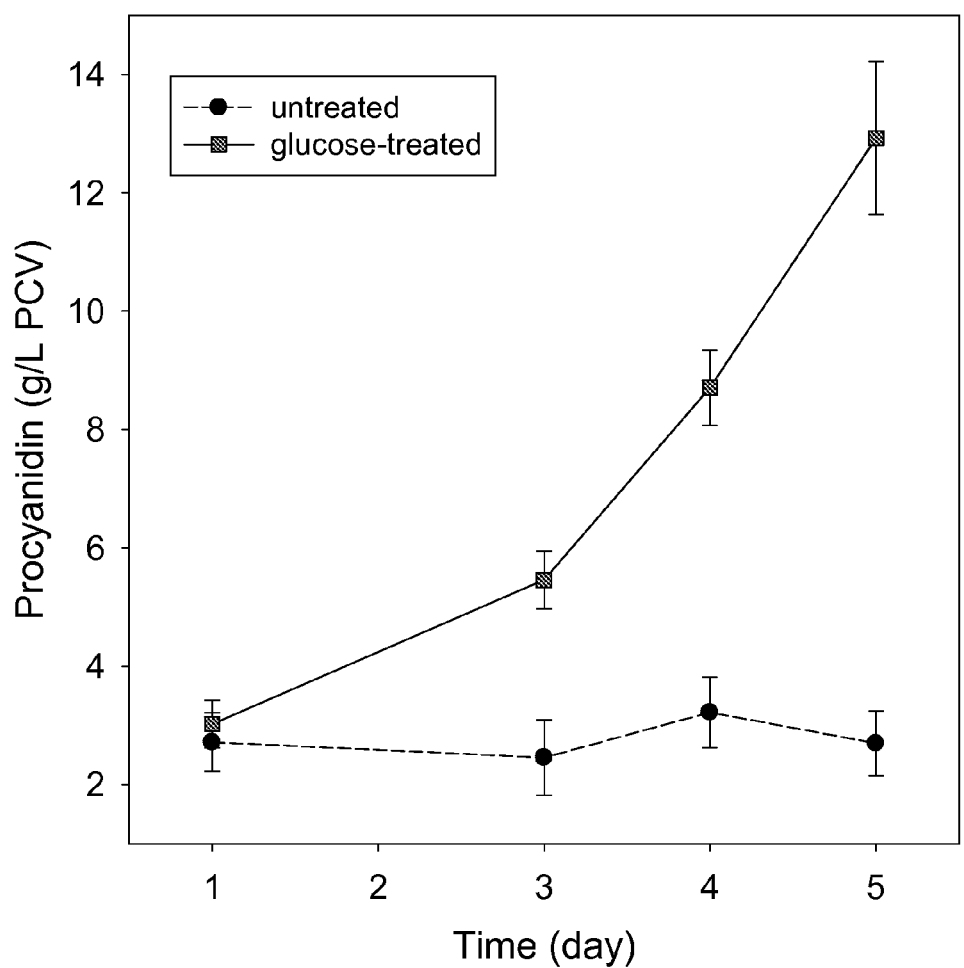
FIG. 7 is a graph showing procyanidin production enhancement over time in cell line MX1440-3496 due to supplemental glucose addition.

All the flasks were sampled and their PCV, RI and procyanidin production were measured at day 1, 3, 4, 5 and 6 post glucose addition. The untreated flasks showed no significant change of RI and slight increase of PCV from 45% to 53±3.6%. Their production stayed at 2.83±1.17 g/L PCV at day 6 post treatment. In contrast, the treated flasks showed an increase in PCV to 53±2.7% at day 6, steadily increasing. RI dropped significantly at a rate of 0.6 to 0.8 units of RI per day, going from 6±1.1 at day 0 to 2.0±1.3 at day 6. Meanwhile, their production also increased from 2.42±1.93 g/L PCV prior to glucose addition to 12.93±2.24 g/L PCV at day 5. The glucose treatment resulted in increased procyanidin production and these production characteristics represent a significant improvement for a cell culture process for procyanidin production as shown in FIG. 7.

Example 12

Scale-up of Cocoa Suspension Culture

A common problem in the use of plant cell cultures is obtaining consistent production of target products (Kim et al., *Biotechnol Prog.* 20(6) 1666, 2004). Therefore, a key for successful large-scale plant cell culture is to maintain stable productivity. A process to scale-up suspensions of cocoa cell cultures from 125 ml flasks to 500 ml flasks was successfully conducted, as cocoa cell growth and production were very consistent and stable under the scaled-up conditions. Average PCV of selected cell lines was 45~55% for seven days, which was about 2.5 times greater than the initial PCV level of 20%. Larger-scale flask cultures were grown in maintenance medium of Medium VIII on a gyratory shaker at 100 rpm under dark conditions. Every seven days of culture, biomass, sugar concentration in medium, and procyanidin productivity were measured.

2.7 L of cacao cells were inoculated into a 6.5 L bioreactor (working volume=5.0 L) and cultivated for seven days under 0.2 vvm (volume of gas per volume of culture per minute) of air flow rate, 100 rpm agitation speed and 23° C. vessel temperature. Biomass increased very slowly and lag phase lasted four days. High inoculation volume was an issue for the cells because this could limit nutrient availability and also make it difficult for uniform mixing of the cells. Ideally starting inoculum volume should be between 25 and 40% PCV. One of the important factors that affects biomass concentration and specific productivity is the gas exchange of dissolved oxygen (DO) concentration and dissolved gaseous metabolites such as $CO_2$ (Dicosmo & Misawa, "*Plant Cell Culture Secondary Metabolism*", 1996, pp44). In flask cultures, it is impossible to control the dissolved oxygen and gaseous metabolites, but controlling them in a reactor culture is feasible. In this example, DO level dropped gradually, which was a good indicator of cellular metabolism.

Example 13

Large-scale Separation From Suspended Cell Cultures

The lyophilized biomass recovered from 10 L of cocoa suspension cell cultures is mixed with 80% methanol at a ratio of 1:1 of the volume of biomass and stirred at room temperature for 1 hour. This is filtered under vacuum in a Buchner funnel through filter paper. Extraction is repeated at least three times. Each methanol extract is collected, pooled and concentrated at 40° C. under reduced pressure to reduce the volume of the methanol extract to 30% of original. The concentrated methanol extract is added to dichloromethane for liquid-liquid extraction and the dichloromethane layer extract is collected, pooled and concentrated at a ratio of 25% at room temperature under reduced pressure. The dried extract is dissolved in methanol, dropped into distilled water and left at 0° C. for two days to obtain precipitate.

The actual yield of pre-purified procyanidin from the dried cells ranges between 10~20% with 50~60% purity. For efficient removal of impurities, further purification is performed by Waters prep-LC (Milford, Mass., USA) using a C18 and a silica column and the purity will be increased up to over 99% after the prep-LC purification process. To obtain the target compound of procyanidin in high purity, the additional process of crystallization can be employed.

Example 14

Comparison of Polyphenols and Procyanidins Produced from Cell Cultures of *Theobroma Cacao* and Cocoa Beans Extraction of Crude Proanthocyanidins from Suspension Cultures The biomass recovered from 1 L of *Theobroma cacao* suspension cell cultures was lyophilized to give 14.0 g of dried cacao cells using Labconco freeze-dryer. The dried powder was extracted with 250 mL of mixed aqueous acetone (70% v/v) for 30 minutes. The aqueous solution was centrifuged at 3500 rpm for 15 minutes and supernatant removed. The solid residue was extracted a second time in the same manner. The supernatants from the two extractions were combined together and then evaporated by rotary evaporator under partial vacuum at 40° C. The concentrated aqueous residue was frozen at −20° C. and dried using Labconco freeze-dryer to give thick yellow crude extract. The yields of crude procyanidins from the dried cell weight were determined by the acid butanol hydrolysis method described in Example B and ranged between 10-15%.

Extraction of Crude Proanthocyanidins from Non-fermented Raw Cocoa Beans

Unfermented raw cocoa beans were obtained from the Raw Harmony (Los Angeles, Calif.). Crude procyanidins were extracted from 5 g of ground dried, non-fermented beans or ground, defatted, non-fermented cocoa beans. Extraction was similar to the procedure used for suspension cell cultures described above except that 50 mL of aqueous acetone (70% v/v) was used for each extraction step and extraction was repeated three times. The combined extracts were centrifuged at 3500 rpm for 15 minutes. The supernatant was decanted and then evaporated to remove solvent under partial vacuum at 40° C. The concentrated aqueous residue was frozen at −20° C. and dried using Labconco freeze-dryer to give reddish purple crude extract. The yields of crude procyanidins as estimated by the acid butanol hydrolysis assay described in Example 8 ranged between 10-13%.

High Performance Liquid Chromatography (HPLC) Analysis of Procyanidins

HPLC analysis of procyanidins was performed by normal phase HPLC system consisting of a Waters 2795 separation module, the Waters 996 PDA detector and the Waters 474 scanning fluorescence detector. Characterization and separation conditions of procyanidins in *Theobroma cacao* cell extract and raw cocoa bean extract obtained using Develosil Diol column (250×4.6 mm ID, 5µ particle size) adapted from Kelm et al. (U.S. Pat. Appl. No. 2007075020) which describes an improved process for polar protic monomers and/or oligomers. The binary mobile phase consists of solvent (A), acetonitrile: acetic acid (98:2, v/v) and solvent (B), methanol: water: acetic acid (95:3:2, v/v/v). A linear gradient elution was performed at 30° C. with 0.8 mL/min flow rate as follows: 0-35 minutes, 100-60% A; 35-40 minutes, 60% A; 40-45 minutes, 60-100% A. Separations of procyanidins was monitored by fluorescence detection (excitation wavelength at 276 nm, emission wavelength at 316 nm), UV detection at 280 nm. (Lazarus et al., *J. Agric. Food Chem.* 47: 3693, 1999).

FIG. 8 shows chromatograms of unfermented cocoa bean extract (FIG. 8A) and *Theobroma cacao* cell suspension extract (FIG. 8B) by fluorescence detector. In agreement with the chromatographic separation described by Kelm et al. (U.S. Pat. Appl. No. 2007075020), the unfermented cocoa bean extract consists of up to dodecamer (degree of polymerization=12). This example confirms that procyanidin extracts from cell cultures of *Theobroma cacao* also have the same profile as that reported for beans. FIG. 9 shows the UV absorbance chromatograms of the unfermented cocoa bean extracts (FIG. 9A) and *Theobroma cacao* cell culture extracts (FIG. 9B). This detection mode allows the detection of caffeine and theobromine and the results of this experiment demonstrate that while the extracts from beans show the presence of these two compounds in the extract they are not detected in the extracts of the cell cultures.

Thus, this example shows that cell cultures of *Theobroma cacao* are able to produce procyanidins identical to those in cocoa beans while they do not produce the undesirable compounds caffeine and theobromine. Further, the extraction procedure described here for cell cultures does not require the use of solvents such as hexanes which would be required for the defatting of cocoa beans. Thus, procyanidin extracts derived from cell cultures of *Theobroma cacao* would not have residues of toxic solvents such as hexanes.

Example 15

Antioxidant Activity of Procyanidin Extracts from Cacao Cell Suspension Cultures This example describes the ways to test for antioxidant activity of procyanidins extracted from cacao cells cultured by methods described in the above examples.

Evidence in the literature suggests a relationship between the health promoting properties of cacao procyanidins and the antioxidant properties of these compounds. It is generally believed that these antioxidants affect certain oxidative and free radical processes involved with some types of tumor promotion and LDL oxidation in cardiovascular diseases. Thus, measuring the antioxidant potential of the cacao procyanidins is a reasonable way to determine the effectiveness of these compounds in preventing human diseases such as cancers and heart disease to enable the use of these compounds in compositions with health promoting properties. Similarly, antioxidants are believed to help maintain a younger looking skin with fewer wrinkles and thus, the cacao procyanidins can be used in cosmetic compositions.

The antioxidant capacity of polyphenolic compounds such as cacao procyanidins are measured by a number of procedures known in the art. The most popular method is the Oxygen Radical Absorbance Capacity (ORAC) method (Cao G, Alessio H, Cutler R (1993). "Oxygen-radical absorbance capacity assay for antioxidants" *Free Radic Biol Med* 14 (3): 303-11). The assay measures the oxidative degradation of the fluorescent molecule (either beta-phycoerythrin or fluorescein) after being mixed with free radical generators such as azo-initiator compounds. Azo-initiators are considered to produce peroxyl free radical by heating, which damages the fluorescent molecule, resulting in the loss of fluorescence. Antioxidants are able to protect the fluorescent molecule from oxidative degeneration. The degree of protection will be quantified using a fluorometer. Fluorescein is currently used most as a fluorescent probe. Equipment that can automatically measure and calculate the capacity is commercially available (Biotek, Roche Diagnostics).

The fluorescent intensity decreases as the oxidative degeneration proceeds, and this intensity is typically recorded for 35 minutes after the addition of the azo-initiator (free radical generator). The degeneration (or decomposition) of fluorescein that is measured as the fluorescence delay becomes less prominent by the presence of antioxidants. Decay curves (fluorescence intensity vs. time) are recorded and the area between two decay curves (with or without antioxidant) is calculated. Subsequently, the degree of antioxidant-mediated protection is quantified using the antioxidant trolox (a vitamin E analogue) as a standard. Different concentrations of trolox are used to make a standard curve, and test samples are compared to this. Results for test samples (foods) are reported as "trolox equivalents" or TE.

TABLE 1

Composition of media I-XXXIV (Recipes for stock solutions are provided in Table 2.

| | I<br>TC723 | II<br>TC726 | III<br>TC727 | IV<br>TC768 | V<br>TC769 | VI<br>TM783 | VII<br>TC784 | VIII<br>TC786 | IX<br>TC787 |
|---|---|---|---|---|---|---|---|---|---|
| MS Medium (Phytotech Catalog # M519) (g/L) | | | | | | | | | |
| MS Vitamins 1000X Stock Solution (Phytotech Catalog # M533) (mL/L) | | | | | | | | | |
| DKW Macro Elements A 10X Stock Solution (mL/L) | 100.0 | | | 100.0 | 100.0 | | | 100.0 | |
| DKW Macro Elements B 10X Stock Solution (mL/L) | 100.0 | | | 100.0 | 100.0 | | | 100.0 | |

TABLE 1-continued

Composition of media I-XXXIV (Recipes for stock solutions are provided in Table 2.

| | | | | | | | | | |
|---|---|---|---|---|---|---|---|---|---|
| DKW Micro Elements 100X Stock Solution (mL/L) | 10.0 | | | 10.0 | 10.0 | | | 10.0 | |
| DKW Salts (Phytotech Catalog # D190) (g/L) | | | | | | | | | |
| WPM Salts (Sigma-Aldrich Catalog # M6774) (g/L) | | 2.3 | 2.3 | | | | | | |
| CP Salts (Sigma-Aldrich Catalog # C6798) (g/L) | | | | | | | | 4.5 | |
| SH Salts (Phytotech Catalog # S816) (g/L) | | | | | 3.2 | 3.2 | | | |
| QL Salts (Phytotech Catalog # Q673) (g/L) | | | | | | | | | |
| B5 Major Salts IM1 medium 10X Stock Solution (mL/L) | | | | | | | | | |
| MS Minor Salts MM medium 1000X Stock Solution (mL/L) | | | | | | | | | |
| MS Salts (Phytotech Catalog # M524) (g/L) | | | | | | | | | |
| MM/IM1 Vitamins 1000X Stock Solution (mL/L) | | | | | | | | | |
| NN Vitamins 1000X Stock Solution (Phytotech Catalog # N608) (mL/L) | | | | | | 1.0 | 1.0 | | |
| DKW Vitamins 1000X Stock Solution (mL/L) | 1.0 | | | 1.0 | 1.0 | | | 1.0 | |
| B5 Vitamins Stock Solution (Phytatech Catalog # G249) (mL/L) | | 1.0 | 1.0 | | | | | | 1.0 |
| Dicamba (mg/L) | | | | | | 0.5 | | | |
| 2,4-D (mg/L) | 2.0 | 2.0 | 2.0 | 1.0 | | 0.5 | | 2.0 | 1.0 |
| 2iP (mg/L) | | | | | | 0.5 | 0.5 | | 0.05 |
| IAA (mg/L) | | | | | | 10.0 | | | 4.0 |
| NAA (mg/L) | | | | | | | 0.5 | | |
| Kinetin (mg/L) | | | 0.3 | | | | | | |
| TDZ (mg/L) | 0.005 | | | 0.005 | 0.005 | | | 0.005 | |
| BA (mg/L) | | 0.05 | | | | | | | |
| Sucrose (g/L) | | | | | | 20.0 | | | 15.0 |
| D-Glucose (g/L) | 20.0 | 20.0 | 20.0 | 20.0 | 20.0 | | 20.0 | 20.0 | 15.0 |
| Coconut water (mL/L) | | | 50.0 | | | | | | |
| L-Glutamine (mg/L) | 250.0 | | | 250.0 | 250.0 | 800.0 | 800.0 | 250.0 | 800.0 |
| Myo-Inositol (mg/L) | 100.0 | | | 100.0 | 100.0 | | | 100.0 | 100.0 |
| Glycine (mg/L) | | | | | | | | | 2.0 |
| Iron Solution 1000X Stock Solution (mL/L) | 1.0 | | | 1.0 | 1.0 | | | 1.0 | |

TABLE 1-continued

Composition of media I-XXXIV (Recipes for stock solutions are provided in Table 2.

| | | | | | |
|---|---|---|---|---|---|
| Phytagel (g/L) | 2.0 | 2.2 | 2.2 | 2.0 | 2.0 |
| Agar (g/L) | | | | | |
| IBA (mg/L) | | | | | |
| Casein Enzymatic Hydrolysate (mg/L) | | | | | |

| | X TC788 | XI TC810 | XII TM812 | XIII TC815 | XIV TC819 | XV TC822 | XVI TC823 | XVII TC824 | XVIII TC825 |
|---|---|---|---|---|---|---|---|---|---|
| MS Medium (Phytotech Catalog # M519) (g/L) | | | | | | | | | |
| MS Vitamins 1000X Stock Solution (Phytotech Catalog # M533) (mL/L) | | | | | | | | | |
| DKW Macro Elements A 10X Stock Solution (mL/L) | | | | 100.0 | | | | | |
| DKW Macro Elements B 10X Stock Solution (mL/L) | | | | 100.0 | | | | | |
| DKW Micro Elements 100X Stock Solution (mL/L) | | | | 10.0 | | | | | |
| DKW Salts (Phytotech Catalog # D190) (g/L | | | | | | | | | |
| WPM Salts (Sigma-Aldrich Catalog # M6774) (g/L) | | | | | 2.3 | | | | |
| CP Salts (Sigma-Aldrich Catalog # C6798) (g/L) | | | | | | | | | |
| SH Salts (Phytotech Catalog # S816) (g/L) | | 3.2 | | | | | | | 3.2 |
| QL Salts (Phytotech Catalog # Q673) (g/L) | 3.56 | | 3.56 | | | 3.56 | 3.56 | 3.56 | |
| B5 Major Salts IM1 medium 10X Stock Solution (mL/L) | | | | | | | | | |
| MS Minor Salts MM medium 1000X Stock Solution (mL/L) | | | | | | | | | |
| MS Salts (Phytotech Catalog # M524) (g/L) | | | | | | | | | |
| MM/IM1 Vitamins 1000X Stock Solution (mL/L) | | | | | | | | | |
| NN Vitamins 1000X Stock Solution (Phytotech Catalog # N608) (mL/L) | | 1.0 | 1.0 | | 1.0 | 1.0 | 1.0 | | |

TABLE 1-continued

Composition of media I-XXXIV (Recipes for stock solutions are provided in Table 2.

|  | | | | | | | | |
|---|---|---|---|---|---|---|---|---|
| DKW Vitamins 1000X Stock Solution (mL/L) | | | | 1.0 | | | | |
| B5 Vitamins Stock Solution (Phytatech Catalog # G249) (mL/L) | 1.0 | | | | | | 1.0 | 1.0 |
| Dicamba (mg/L) | | 0.5 | 0.5 | | 0.5 | 0.5 | 0.5 | |
| 2,4-D (mg/L) | 1.0 | | | 2.0 | | | 2.0 | 2.0 |
| 2iP (mg/L) | 0.05 | 0.5 | 0.5 | | 0.5 | 0.5 | 0.5 | |
| IAA (mg/L) | 4.0 | | | | | | | |
| NAA (mg/L) | | 0.5 | 0.5 | | 0.5 | 0.5 | 0.5 | |
| Kinetin (mg/L) | | | | | | | | |
| TDZ (mg/L) | | | | 0.005 | | | 0.005 | 0.005 |
| BA (mg/L) | | | | | | | | |
| Sucrose (g/L) | 15.0 | 10.0 | 20.0 | | 20.0 | | 10.0 | |
| D-Glucose (g/L) | 15.0 | 10.0 | | 20.0 | | 20.0 | 10.0 | 20.0 |
| Coconut water (mL/L) | | | | | | | | |
| L-Glutamine (mg/L) | 800.0 | 800.0 | 800.0 | 250.0 | 800.0 | 800.0 | 800.0 | 800.0 |
| Myo-Inositol (mg/L) | 100.0 | | | 100.0 | | | | |
| Glycine (mg/L) | 2.0 | | | | | | 2.0 | 2.0 |
| Iron Solution 1000X Stock Solution (mL/L) | | | | 1.0 | | | | |
| Phytagel (g/L) | | | | | | | | |
| Agar (g/L) | | | | | | | | |
| IBA (mg/L) | | | | | | | | |
| Casein Enzymatic Hydrolysate (mg/L) | | | | | | | | |

|  | XIX TC826 | XX TC827 | XXI TC829 | XXII TM434 | XXIII TM784 | XXIV TC1599 | XXV TC1234 | XXVI DC1151 | XXVII TC1248 |
|---|---|---|---|---|---|---|---|---|---|
| MS Medium (Phytotech Catalog # M519) (g/L) | | | | | | 4.43 | | | 4.43 |
| MS Vitamins 1000X Stock Solution (Phytotech Catalog # M533) (mL/L) | | | | | | 1.0 | | | 1.0 |
| DKW Macro Elements A 10X Stock Solution (mL/L) | | | | | | | | | |
| DKW Macro Elements B 10X Stock Solution (mL/L) | | | | | | | | | |
| DKW Micro Elements 100X Stock Solution (mL/L) | | | | | | | | | |
| DKW Salts (Phytotech Catalog # D190) (g/L | | | | | | | | | |

TABLE 1-continued

Composition of media I-XXXIV (Recipes for stock solutions are provided in Table 2.

| | C1 | C2 | C3 | C4 | C5 | C6 | C7 | C8 | C9 | C10 |
|---|---|---|---|---|---|---|---|---|---|---|
| WPM Salts (Sigma-Aldrich Catalog # M6774) (g/L) | 2.3 | 2.3 | 2.3 | | | | | | | |
| CP Salts (Sigma-Aldrich Catalog # C6798) (g/L) | | | | | | | | | | |
| SH Salts (Phytotech Catalog # S816) (g/L) | | | | 3.2 | 3.2 | | | | | |
| QL Salts (Phytotech Catalog # Q673) (g/L) | | | | | | | | | | |
| B5 Major Salts IM1 medium 10X Stock Solution (mL/L) | | | | | | | 100 | | | |
| MS Minor Salts MM medium 1000X Stock Solution (mL/L) | | | | | | | | | 1.0 | |
| MS Salts (Phytotech Catalog # M524) (g/L) | | | | | | | | | 4.3 | |
| MM/IM1 Vitamins 1000X Stock Solution (mL/L) | | | | | | | | | 1.0 | |
| NN Vitamins 1000X Stock Solution (Phytotech Catalog # N608) (mL/L) | | 1.0 | 1.0 | 1.0 | 1.0 | | | | 1.0 | |
| DKW Vitamins 1000X Stock Solution (mL/L) | | | | | | | | | | |
| B5 Vitamins Stock Solution (Phytatech Catalog # G249) (mL/L) | 1.0 | | | | | | | | | |
| Dicamba (mg/L) | | 0.5 | 0.5 | 0.5 | 0.5 | | | | | |
| 2,4-D (mg/L) | 2.0 | | | | | | | 1.5 | | |
| 2iP (mg/L) | | 0.5 | 0.5 | 0.5 | 0.5 | | | | | |
| IAA (mg/L) | | | | | | 2.0 | | | | 2.0 |
| NAA (mg/L) | | 0.5 | 0.5 | 0.5 | 0.5 | | 0.1 | | | |
| Kinetin (mg/L) | | | | | | | | 0.2 | | |
| TDZ (mg/L) | 0.005 | | | | | 0.005 | | | | 0.005 |
| BA (mg/L) | | | | | | | | | | |
| Sucrose (g/L) | | | 10.0 | 20.0 | | | 60.0 | 30.0 | | 20.0 |
| D-Glucose (g/L) | 20.0 | 20.0 | 10.0 | | 20.0 | 20.0 | | | | 20.0 |
| Coconut water (mL/L) | | | | | | | | | | |
| L-Glutamine (mg/L) | 800.0 | 800.0 | 800.0 | 800.0 | 800.0 | 250.0 | | | | 250.0 |
| Myo-Inositol (mg/L) | | | | | | | | | | |
| Glycine (mg/L) | 2.0 | | | | | | | | | |
| Iron Solution 1000X Stock Solution (mL/L) | | | | | | | | | | |
| Phytagel (g/L) | | | | | | | | | | |

TABLE 1-continued

Composition of media I-XXXIV (Recipes for stock solutions are provided in Table 2.

| | | | | | | | |
|---|---|---|---|---|---|---|---|
| Agar (g/L) | | | | | | | 7.0 |
| IBA (mg/L) | | | | 4.0 | | | 4.0 |
| Casein Enzymatic Hydrolysate (mg/L) | | | | | 250.0 | | |

| | XXVIII TC1596 | XXIX TC1632 | XXX TC1633 | XXXI TC1634 | XXXII TC1482 | XXXIII TC1682 | XXXIV TC1701 |
|---|---|---|---|---|---|---|---|
| MS Medium (Phytotech Catalog # M519) (g/L) | 4.43 | 4.43 | 4.43 | 4.43 | | 4.43 | 4.43 |
| MS Vitamins 1000X Stock Solution (Phytotech Catalog # M533) (mL/L) | 1.0 | 1.0 | | | | 1.0 | 1.0 |
| DKW Macro Elements A 10X Stock Solution (mL/L) | | | | | | | |
| DKW Macro Elements B 10X Stock Solution (mL/L) | | | | | | | |
| DKW Micro Elements 100X Stock Solution (mL/L) | | | | | | | |
| DKW Salts (Phytotech Catalog # D190) (g/L | | | | | 5.22 | | |
| WPM Salts (Sigma-Aldrich Catalog # M6774) (g/L) | | | | | | | |
| CP Salts (Sigma-Aldrich Catalog # C6798) (g/L) | | | | | | | |
| SH Salts (Phytotech Catalog # S816) (g/L) | | | | | | | |
| QL Salts (Phytotech Catalog # Q673) (g/L) | | | | | | | |
| B5 Major Salts IM1 medium 10X Stock Solution (mL/L) | | | | | | | |
| MS Minor Salts MM medium 1000X Stock Solution (mL/L) | | | | | | | |
| MS Salts (Phytotech Catalog # M524) (g/L) | | | | | | | |
| MM/IM1 Vitamins 1000X Stock Solution (mL/L) | | | | | | | |
| NN Vitamins 1000X Stock Solution (Phytotech Catalog # N608) (mL/L) | | | | | | | |
| DKW Vitamins 1000X Stock Solution (mL/L) | | | | | 1.0 | | |
| B5 Vitamins Stock Solution (Phytatech Catalog # G249) (mL/L) | | | | | | | |
| Dicamba (mg/L) | | | | | | | |
| 2,4-D (mg/L) | | | | | 2.0 | | |
| 2iP (mg/L) | | | | | | | |
| IAA (mg/L) | 2.0 | | | | | 1.0 | 2.0 |
| NAA (mg/L) | | | | | | | |
| Kinetin (mg/L) | | | | | | | |
| TDZ (mg/L) | 0.005 | 0.005 | 0.005 | 0.005 | 0.005 | 0.005 | 0.005 |
| BA (mg/L) | | | | | | | |
| Sucrose (g/L) | | | | | | | |
| D-Glucose (g/L) | 20.0 | 20.0 | 20.0 | 20.0 | 20.0 | 20.0 | 20.0 |
| Coconut water (mL/L) | | | | | | | |
| L-Glutamine (mg/L) | 250.0 | 250.0 | 250.0 | | 250.0 | 250.0 | 250.0 |
| Myo-Inositol (mg/L) | | | | | 100.0 | | |
| Glycine (mg/L) | | | | | | | |
| Iron Solution 1000X Stock Solution (mL/L) | | | | | | | |

TABLE 1-continued

Composition of media I-XXXIV (Recipes for stock solutions are provided in Table 2.

| | | | | | | |
|---|---|---|---|---|---|---|
| Phytagel (g/L) | | | | | | |
| Agar (g/L) | 7.0 | 7.0 | 7.0 | 7.0 | | |
| IBA (mg/L) | 2.0 | 2.0 | 2.0 | 2.0 | 2.0 | 2.0 |
| Casein Enzymatic Hydrolysate (mg/L) | | | | | | |

TABLE 2

Recipes for Stock Solutions Used in Media Described in Table 1

| Stock Solution Name | Volume | Chemical | Amount | |
|---|---|---|---|---|
| DKW 10X Macro Elements Solution A | 1 L | $NH_4NO_3$ | 14.16 | g |
| | | $Ca(NO_3)_2 \cdot 4H_2O$ | 19.69 | g |
| DKW 10X Macro Elements Solution B | 1 L | $CaCl_2 \cdot 2H_2O$ | 1.49 | g |
| | | $K_2SO_4$ | 15.59 | g |
| | | $MgSO_4 \cdot 7H_2O$ | 7.40 | g |
| | | $KH_2PO_4$ | 2.65 | g |
| DKW 100X Micro Elements Solution | 1 L | $Zn(NO_3)_2 \cdot 6H_2O$ | 1.70 | g |
| | | $MnSO_4 \cdot H_2O$ | 3.34 | g |
| | | $CuSO_4 \cdot 5H_2O$ | 25.0 | mg |
| | | $H_3BO_4$ | 480.0 | mg |
| | | $Na_2MoO_4 \cdot 2H_2O$ | 39.0 | mg |
| Iron Solution 1000X Stock Solution | 1 L | $Na_2EDTA$ (0.5M solution) | 200 | ml |
| | | $FeSO_4 \cdot 7H_2O$ | 27.8 | g |
| DKW 1000X Vitamins Stock Solution | 100 mL | Myo-Inositol | 10.0 | g |
| | | Thiamine-HCl | 0.2 | g |
| | | Nicotinic acid | 0.1 | g |
| | | Glycine | 0.2 | g |
| B5 1000X Vitamin Stock Solution | 50 mL | Myo-Inositol | 5.0 | g |
| | | Nicotinic acid | 50.0 | mg |
| | | Pyridoxine | 50 | mg |
| | | Thiamine | 500.0 | mg |
| B5 Major Salts IM1 10X Stock Solution | 1 L | $(NH_4)_2SO_4$ | 2.68 | g |
| | | $CaCl_2$ | 1.13 | g |
| | | $MgSO_4$ | 2.44 | g |
| | | $KNO_3$ | 25.0 | g |
| | | $NaH_2PO_4$ | 3.0 | g |
| MS Minor Salts MM 1000X Stock Solution | 1 L | $MnSO_4 \cdot H_2O$ | 16.9 | g |
| | | $ZnSO_4 \cdot 7H_2O$ | 8.6 | g |
| | | $H_3BO_4$ | 6.2 | g |
| | | KI | 0.83 | g |
| | | $Na_2MoO_4 \cdot 2H_2O$ | 0.25 | g |
| | | $CuSO_4 \cdot 5H_2O$ | 25.0 | mg |
| | | $CoCl_2 \cdot 6H_2O$ | 25.0 | mg |
| MM/IM1 Vitamins 1000X Stock Solution | 1 L | Biotin | 10.0 | mg |
| | | Calcium pantothenate | 1.0 | g |
| | | Myo-Inositol | 100.0 | g |
| | | Pyridoxine | 1.0 | g |
| | | Thiamine | 1.0 | g |
| | | Pyridine-3-carboxylic acid | 1.0 | g |

We claim:

1. A method of producing a cell suspension culture of cacao cells, comprising:
   growing callus from a *Theobroma cacao* plant on growth medium to form a callus culture;
   identifying and selecting a rapidly growing cell line from the cells of the *Theobroma cacao* callus culture, the rapidly growing cell line selected to produce procyanidins in cell suspension with less than 2% theobromine and/or less than 0.5% caffeine contamination on a dry weight basis; and
   initiating the cell suspension culture by inoculating the rapidly growing cell line into liquid medium and producing in cell suspension procyanidins with less than 2% theobromine and/or less than 0.5% caffeine contamination on a dry weight basis.

2. The method of claim 1, wherein the *Theobroma cacao* plant is a floral explant selected from the group staminode, sepal and petal base explants.

3. The method of claim 1, further comprising growing the cell suspension culture in flasks, any suitable culture vessels, or bioreactors.

4. The method of claim 3, wherein the growing is effected in vessels or bioreactors and in batch, fed-batch or continuous mode.

5. A *Theobroma cacao* cell suspension culture produced by the method of claim 1.

6. The method of claim 1, wherein the growth medium is the liquid media XXXIII listed in Table 1.

7. The method of claim 1, wherein the callus is from a vegetative material.

8. The method of claim 7, wherein the vegetative material is selected from leaves, stems, meristem, nodes, or internodes that are young or mature.

9. The method of claim 1, wherein the step of selecting the rapidly growing cell line includes analyzing the callus culture using high performance liquid chromatography to determine the production of procyanidins.

* * * * *

UNITED STATES PATENT AND TRADEMARK OFFICE
CERTIFICATE OF CORRECTION

| | |
|---|---|
| PATENT NO. | : 8,568,798 B2 |
| APPLICATION NO. | : 13/262456 |
| DATED | : October 29, 2013 |
| INVENTOR(S) | : Venkatramesh et al. |

Page 1 of 2

It is certified that error appears in the above-identified patent and that said Letters Patent is hereby corrected as shown below:

In the Specification

Figure 5A:
FIG. 5 illustrates a butanol-HCl hydrolysis assay for measuring procyanidins. Acid hydrolysis of procyanidins leads to their breakdown to two monomeric forms, (−)-Epicatechin and cyanidin which is pink in color. Intensity of pink color in each sample represents amount of procyanidins obtained in different cell lines (FIG. 5A). The method in FIG. 5A was optimized to a 96-well plate format for rapid screening of samples (FIG. 5B). The cyanidin absorption is at 520 nm and the epicatechin absorption is at 280 nm (FIG. 5C); quantification is calculated from the cyanidin absorbance value.
Figure 5B:
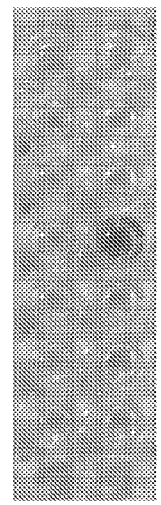
Figure 5C:
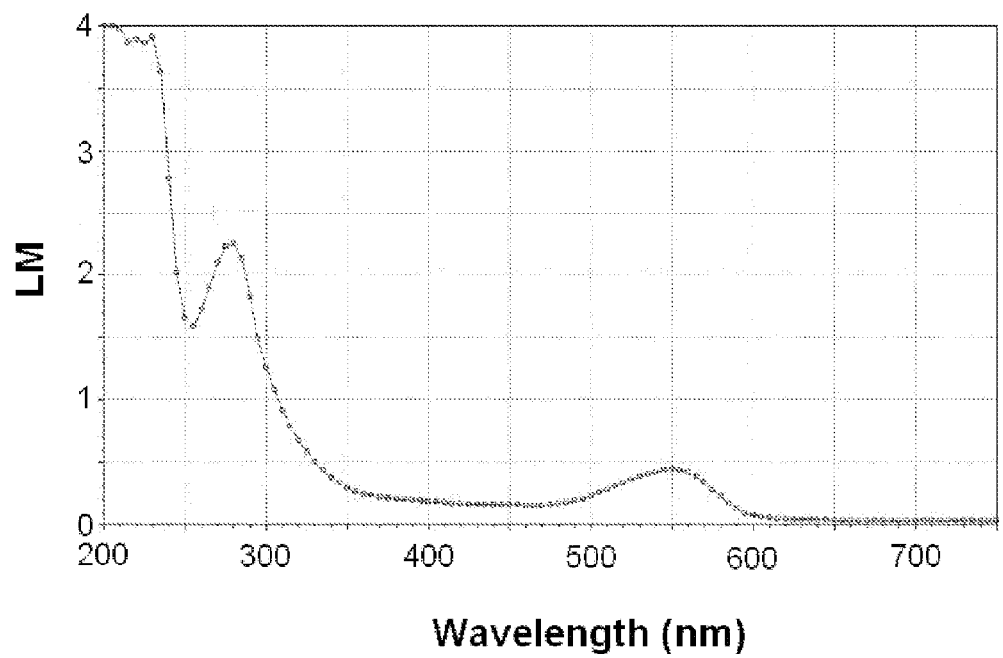

Column 4
Line 64, change "FIG. 5 illustrates" to --FIGS. 5A-5C illustrate--

Column 5
Line 9, change "that represent" to --represent--
Line 16, change "FIG. 8 is" to --FIGS. 8A and 8B are--
Line 23, change "FIG. 9 is" to --FIGS. 9A and 9B are--
Line 26, change "FIG. 10 is" to --FIGS. 10A-10E are--

Column 6
Line 37, change "epicatechin, leucocyanidin" to --epicatechin, and leucocyanidin--

Column 7
Line 21, change "cell-culture generated" to --cell culture-generated--

Column 11
Line 1, change "In case" to --In the case--
Line 34, change "clean can" to --clean and can--

Column 12
Line 66, change "such aeration rate, rheological properties" to --such as aeration rate and rheological properties--

Column 14
Line 57, change "thickeners sweeteners" to --thickeners or sweeteners--

Signed and Sealed this
Fourteenth Day of July, 2015

Michelle K. Lee
*Director of the United States Patent and Trademark Office*

CERTIFICATE OF CORRECTION (continued)
U.S. Pat. No. 8,568,798 B2

Column 15
Line 35, change "allows for" to --allow for--

Column 17
Line 4, change "everyday" to --every day--

Column 24
Line 36, change "Example Band" to --Example 8 and--

Column 25
Line 7, change "FIG. 8 shows" to --FIGS. 8A and 8B show--
Line 15, change "FIG. 9 shows" to --FIGS. 9A and 9B show--